United States Patent [19]
Lee et al.

[11] Patent Number: 5,525,604
[45] Date of Patent: Jun. 11, 1996

[54] 4-AMINOPYRIMIDINE DERIVATIVES

[75] Inventors: Sung J. Lee, Clarks Summit, Pa.;
Yoshitaka Konishi, Osaka, Japan;
Orest T. Macina, Clarks Summit, Pa.;
Kigen Kondo, Osaka, Japan; Dingwei T. Yu, Easton; Tamara A. Miskowski, Clarks Summit, both of Pa.

[73] Assignee: Ono Pharmaceutical Co., Ltd., Osaka, Japan

[21] Appl. No.: 295,377

[22] Filed: Aug. 24, 1994

Related U.S. Application Data

[63] Continuation-in-part of Ser. No. 111,906, Aug. 26, 1993, abandoned.

[51] Int. Cl.$^6$ .................. C07D 401/04; C07D 401/06; C07D 401/12; A61K 31/505
[52] U.S. Cl. ............... 514/256; 514/212; 514/252; 514/269; 514/273; 514/275; 544/333; 544/295; 544/296; 544/238; 544/326; 544/327; 544/328; 544/329; 544/323; 544/324; 544/325; 544/319; 544/320; 544/321; 540/601
[58] Field of Search ...................... 544/324, 327, 544/328, 333, 238, 323, 320; 514/275, 256, 212, 252, 269, 273; 540/601

[56] References Cited

U.S. PATENT DOCUMENTS

| | | | |
|---|---|---|---|
| 3,992,320 | 11/1976 | Schneider et al. | 252/429 |
| 3,992,380 | 11/1976 | Lesher et al. | 544/328 |
| 4,018,770 | 4/1977 | Lesher et al. | 260/256.4 |
| 4,032,523 | 6/1977 | Lesher et al. | 260/256.4 |
| 5,250,530 | 10/1993 | Giencke et al. | 514/256 |
| 5,318,975 | 6/1994 | Lis | 514/275 |

FOREIGN PATENT DOCUMENTS

94/07867  4/1994  WIPO.

*Primary Examiner*—John M. Ford
*Attorney, Agent, or Firm*—Watson Cole Stevens Davis

[57] ABSTRACT

A 4-aminopyrimidine of the formula (I):

$$\text{(R}_3\text{—A)}l \overset{\displaystyle HN^{Y-R^2}}{\underset{\displaystyle N}{\bigg|}} \overset{\displaystyle}{\underset{\displaystyle Z-R^1}{N}}$$ (I)

wherein
A is a bond, C1–4 alkylene or C1–4 oxyalkylene;
Y is a bond, C1–4 alkylene, C1–4 alkyleneoxy, C1–4 alkoxyphenylene or phenyl(C1–4)alkylene;
Z is a bond or vinylene;
R1 is 4–15 membered heterocyclic ring containing one or two nitrogen atom;
R2 is (i) 4–15 membered heterocyclic ring containing one or two nitrogen, one or two of oxygen or one sulfur atom,
(ii) C4–15 carbocyclic ring,
(iii) C1–4 alkoxy,
(iv) hydroxy(C1–4 alkoxy) or
(v) hydroxy;
R3 is (i) 4–15 membered heterocyclic ring containing one or two nitrogen, one oxygen, one sulfur, or one nitrogen and one sulfur atom,
(ii) C4–15 carbocyclic ring,
(iii) formula:

$$CH_2=CH(X)-$$

wherein
X is halogen.
(iv) hydrogen.
l is 1 or 2.
and some compounds are excluded.
and acid addition salts thereof, salts thereof; have inhibitory effect on cGMP-PDE, or additionally on TXA2 synthetase.

38 Claims, No Drawings

4-AMINOPYRIMIDINE DERIVATIVES

This application is a continuation-in-part of U.S. Ser. No. 08/111,906, filed Aug. 26, 1993, now abandoned, the entire disclosure of which is incorporated herein by reference.

FIELD OF THE INVENTION

The present invention relates to novel 4-aminopyrimidine derivatives. More particularly, this invention relates to:
(i) 4-aminopyrimidine derivatives of the following formula (I):

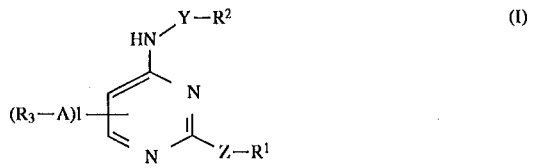

wherein all of the symbols have the same meanings as described hereinafter, and the pharmaceutically acceptable acid addition salts thereof and the pharmaceutically acceptable salts thereof,
(ii) processes for the preparation thereof,
(iii) inhibitors of cyclic guanosine 3',5'-monophosphate phosphodiesterase, or additionally of thromboxane A2 synthetase containing them, and
(iv) methods of prevention and treatment of mammals, including humans, by administering an effective amount of the compounds of the formula (I), the pharmaceutically acceptable acid addition salts thereof and the pharmaceutically acceptable salts thereof to the patient to be treated.

BACKGROUND OF THE INVENTION

Cyclic guanosine 3',5'-monophosphate (abbreviated as cGMP hereafter) was found in urine in rats by D. F. Ashman in 1963. Till now, it has been known that cGMP is distributed broadly in tissues of many animals including human beings. cGMP is biosynthesized from guanosine triphosphate (GTP) by the action of guanylate cyclase.

cGMP has been experimentally confirmed to have various physiological activities. For example, cGMP induces the relaxation of heart muscle and of smooth muscle. Further, it is related to the formation of neuronal synapses, and it acts as a trigger of cell proliferation and it induces the proliferation of lymphocyte.

cGMP is metabolized to physiologically inactive 5'-GMP by the action of cGMP phosphodiesterase (abbreviated as cGMP-PDE hereafter).

Accordingly, the inhibition of the action of cGMP-PDE is considered to be useful for the prevention and/or treatment of diseases induced by enhancement of the metabolism of cGMP, such as hypertension, heart failure, myocardial infarction, angina, atherosclerosis, cardiac edema, pulmonary hypertension, renal insufficiency, nephrotic edema, hepatic edema, asthma, bronchitis, dementia, immunodeficiency.

On the other hand, thromboxane A2 (abbreviated as TXA2 hereafter) was found as a constituent of the arachidonate cascade, in platelets by M. Hamberg in 1975, TXA2 is biosynthesized from arachidonic acid released from cell membrane via prostaglandin G2 and prostaglandin H2, and rapidly metabolized to inactive thromboxane B2. TXA2 is known to induce platelet aggregation and to contract smooth muscle, particularly blood vessel muscle and bronchial muscle. TXA2 synthetase was isolated and purified from microsome in platelets.

Accordingly, the inhibition of TXA2 synthetase decreases the biosynthesis of TXA2, and is useful for the prevention and/or treatment of inflammation, hypertension, thrombosis, arteriosclerosis, cerebral apoplexy, asthma, myocardial infarction, cardiostenosis, cerebral infarction, etc.

It is considered that almost any disease occurs by the complex interaction of plural mechanisms. Accordingly, the inhibition of any one of the plural mechanism may not be adequate to treat a disease. A medicament inhibiting as many mechanisms as possible, which induce the disease, is considered to be effective and ideal.

Especially, it is very useful for the prevention and/or treatment of diseases induced by platelet aggregation, e.g. angina pectoris, heart failure, pulmonary hypertension and various kinds of renal diseases to have inhibitory active on both cGMP PDE and TXA2 synthetase.

RELATED ARTS

Up to now, some compounds have been known as cGMP-PDE inhibitors, for example,

Zaprinast

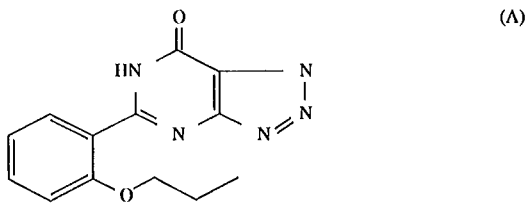

AR-L 57

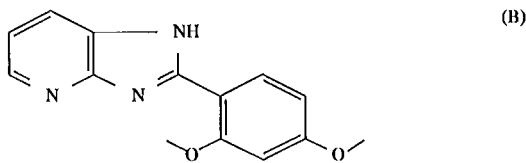

MY-5445

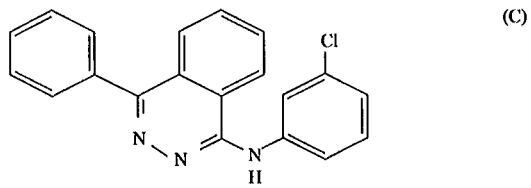

Furthermore, some TXA2 synthetase inhibitors have been known, for example,

OKY-046

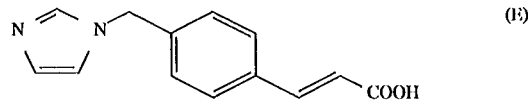

ONO-1581

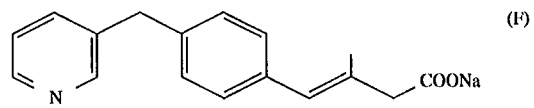

Many derivatives containing an imidazole or pyridine ring as the basic skeleton have been proposed. However, there appears to be no TXA2 synthetase inhibitor having both the said ring and pyrimidine ring.

On the other hand, many compounds having a pyrimidine ring as the skeleton, which are not known to have inhibitory activity on cGMP-PDE and/or on TXA2 synthetase, have been proposed.

On the other hand, some compounds similar to the present invention exist. For example, EP-407899 (i.e. U.S. Pat. No. 5,250,530) disclosed that: 4-aminopyrimidine of the formula (G):

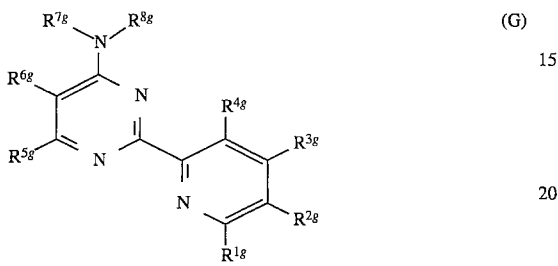

wherein

R1g is hydrogen, (C1–C6)alkyl, (C1–C4)alkoxy-(C1–C4)alkyl, and (C3–C7)cycloalkyl-(C1–C4)alkyl, where the last two radicals can be up to trisubstituted in the cycloalkyl moiety by (C1–C4)alkyl, or is a group R7gR8gN-(C1–C4)alkyl, phenyl, phenoxy-(C1–C4)alkyl, phenylmercapto-(C1–C4)alkyl, phenyl-(C1–C4)alkyl and phenoxyphenoxy-(C1–C4)alkyl, where the last five radicals can be up to trisubstituted in the phenyl moiety by halogen, nitro, cyano, (C1–C4)alkyl, (C1–C4)alkoxy, (C1–C4)alkylthio, (C1–C4)haloalkyl or (C1–C4)haloalkoxy, R2g, R3g and R4g independently of one another are hydrogen, (C1–C6)alkyl or phenyl, where the phenyl radical can be up to trisubstituted by halogen, nitro, cyano, (C1–C4)alkyl, (C1–C4)alkoxy, (C1–C4)alkylthio, (C1–C4)haloalkyl or (C1–C4)haloalkoxy, R5g is hydrogen, (C1–C6)alkyl, (C3–C7)cycloalkyl or (C3–C7)cycloalkyl-(C1–C4)alkyl, where the last two radicals can be up to trisubstituted in the cycloalkyl moiety by (C1–C4)alkyl, or (C1–C4)haloalkyl, (C1–C4)alkoxy, (C1–C 4)alkylthio, (C1–C4)alkoxy-(C1–C4)alkyl, a group R7gR8gN-, (C1–C4)alkylthio-(C1–C4)alkyl, a group R7gR8gN-(C1–C4)alkyl, halogen, (C2–C6)alkenyl, (C2–C6)alkynyl, phenyl, phenoxy, phenyl(C1–C4)alkyl, phenoxy(C1–C4)alkyl, phenylmercapto-(C1–C4)alkyl, phenylmercapto, phenyl-(C1–C4)alkoxy or phenyl-(C1–C4)alkylthio, where the last eight radicals can be up to trisubstituted in the phenyl moiety by halogen, nitro, cyano, (C1–C4)alkyl, (C1–C4)alkoxy, (C1–C4)haloalkyl or (C1–C4)haloalkoxy;

R6g is hydrogen, (C1–C4)alkyl, (C1–C4)alkoxy, (C2–C6)alkenyloxy, (C2–C6)alkynyloxy, (C1–C4)alkylthio, halogen or phenyl, where the phenyl radical can be up to trisubstituted by halogen, nitro, cyano, (C1–C4)alkyl, (C1–C4)alkoxy, (C1–C4)alkylthio, (C1–C4)haloalkyl or (C1–C4)haloalkoxy, or R5g and R6g together form a polymethylene chain of the formula —(CH2)mg with mg being 3–4 and R7g and R8g independently of one another are hydrogen, (C1–C6)alkyl, (C1–C4)alkoxy-(C1–C6)alkyl, hydroxy-(C1–C6)alkyl, (C1–C4)alkylthio-(C1–C6)alkyl, R9gR10gN-(C1–C6)alkyl, (C3–C6)alkenyl, (C3–C6)alkynyl, (C3–C7)cycloalkyl or (C3–C7)cycloalkyl-(C1–C4)alkyl, where the last two radicals can be up to trisubstituted in the cycloalkyl moiety by (C1–C4)alkyl; or are formyl, phenyl or phenyl-(C1–C4)alkyl, where the last two radicals can be up to trisubstitued in the phenyl moiety by halogen, nitro, cyano, (C1–C4)alkyl, (C1–C4)alkoxy, (C1–C4)alkylthio, (C1–C4)haloalkyl or (C1–C4)haloalkoxy; or the two radicals R7g and R8g together with the nitrogen atom to which they are bonded stand for an unsubstituted or up to tetrasubstituted 5- to 7-membered, saturated or unsaturated heterocycle which has 1 to 3 identical or different hetero atoms, preferably the hetero atoms nitrogen, oxygen and/or sulfur, and the substituent (C1–C4)alkyl;

R9g and R10g independently of one another are hydrogen, (C1–C6)alkyl, (C3–C6)alkenyl, (C3–C6)alkynyl, (C3–C7)cycloalkyl or (C3–C7)cycloalkyl(C1–C4)alkyl, where the last two radicals can be up to trisubstituted in the cycloalkyl moiety by (C1–C4)alkyl; or are formyl, phenyl, phenyl(C1–C4)alkyl, where the last two radicals can be up to trisubstituted in the phenyl moiety by halogen, nitro, cyano, (C1–C4)alkyl, (C1–C4)alkoxy, (C1–C4)alkylthio, (C1–C4)haloalkyl or (C1–C4)haloalkoxy;

or the two radicals R9g and R10g together with the nitrogen atom to which they are bonded stand for an unsubstituted or up to tetrasubstituted 5- to 7-membered, saturated or unsaturated heterocycle which has 1 to 3 identical or different hetero hetero atoms, preferably the hetero atoms nitrogen, oxygen and/or sulfur, and the substituent (C1–C4)alkyl;

and the acid addition salts thereof possess fungicidal properties.

U.S. Pat. No. 4,018,770 disclosed that:

pyridylpyrimidine derivatives of the formula (H):

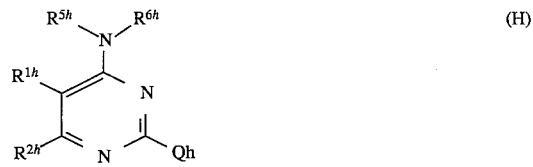

where Qh is 4, 3- or 2-pyridinyl or 4-, 3- or 2-pyridinyl having one or two lower-alkyl substituents or N-oxide thereof, Q'h is hydroxy, halo, hydrazino or amino, R1h is hydrogen, lower-alkyl or cyano, and R2h is hydrogen, lower-alkyl, hydroxy or halo.

R5h is hydrogen, lower-alkyl or lower-hydroxyalkyl and,

R6h is lower-alkyl or lower-hydroxyalkyl are useful for anti-allergic agent.

U.S. Pat. No. 3,992,380 disclosed that:

pyrimidine derivatives of the formula (J):

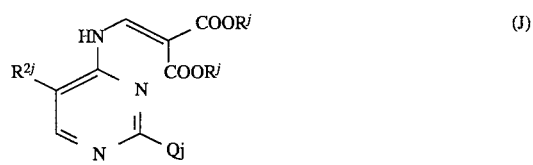

wherein Qj is 4(or 3-)pyridinyl or 4(or 3-)pyridinyl having one or two lower-alkyl substituents, R2j is hydrogen or lower-alkyl, Rj is lower-alkyl.

is useful for the intermediate of pyrido[2,3-d]pyrimidine derivative having antibacterial activity.

WO 94/07867 disclosed that:

Compounds of formula (K):

wherein R1k is hydrogen, CF3, (C1–C6)alkyl, (C1–C6)alkyl-S-(C1–C6)alkyl, (C1–C6)alkyl-SO(C1–C6)alkyl, (C1–C6)alkyl-SO2-(C1–C6)alkyl, hydroxy(C1–C6)alkyl dihydroxy-(C1–C6)alkyl, (C1–C6)alkoxy, (C1–C6)alkoxycarbonyl-(C1–C6)alkyl, aryl selected from phenyl and naphthyl, aryl-(C1–C6)alkyl wherein the aryl moiety is selected from phenyl and naphthyl, (1–C6)alkoxycarbonylaryl wherein the aryl moiety is selected from phenyl and naphthyl, selected from phenyl and naphthyl, aryl-(C1–C6)alkoxy wherein the aryl moiety is heteroaryl selected from pyridyl, furyl, tetrahydrofuryl, thienyl, imidazolyl, pyrazolyl, triazolyl, thiazolyl, oxazolyl, benzothiazolyl, benzofuranyl, and benzothienyl; heteroaryl-(C1–C6)alkyl wherein heteroaryl is defined as above, or heteroaryl-(C1–C6)alkoxy wherein heteroaryl is defined as above, and wherein said aryl and heteroaryl groups, the aryl moieties of said aryl-(C1–C6)alkyl, (C1–C6)alkoxycarbonylaryl and aryl-(C1–C6)alkyloxy and the heteroaryl moiety of said heteroaryl-(C1–C6)alkyl may optionally be substituted with one or more substituents independently selected from chloro, bromo, (C1–C6)alkyl, (C1–C6)alkoxy, —S-(C1–C6)alkyl, —SO-(C1–C6)alkyl, —SO2-(C1–C6)alkyl, hydroxy-(C1–C6)alkyl and trifluoromethyl;

or R1k is a group of the formula

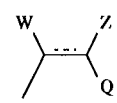

wherein the dotted line represents an optional double bond, W, Q, and Z are independently selected from hydrogen, (C1–C6)alkyl and trifluoromethyl, phenyl, furyl, thiazolyl and thienyl, wherein said phenyl, furyl, triazolyl, thiazolyl and thienyl may optionally be substituted with one or more substituents independently selected from (C1–C6)alkyl, (C1–C6)alkoxy, trifluoromethyl and hydroxy;

or R1k is a group of the formula —CO-R6k, wherein R6k is hydrogen, (C1–C6)alkyl, aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl and benzothienyl, wherein said aryl and heteroaryl groups may optionally be substituted with one or more substituents independently selected from chloro, bromo, nitro, trifluoromethyl, (C1–C6)alkoxy, —S-(C1–C6)alkyl, —SO-(C1–C6)alkyl and —SO2-(C1–C6)alkyl;

or R1k is a group of the formula

—CH(R7k)—O—Y, wherein R7k is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents, preferably with from zero to two substituents, independently selected from chloro, bromo, (C1–C6)alkyl, (C1–C6)alkoxy, —S-(C1–C6)alkyl, —SO-(C1–C6)alkyl, —SO2-(C1–C6)alkyl and trifluoromethyl, and Y is hydrogen, benzyl, acetyl, benzoyl, aryl selected from phenyl and naphthyl, heteroaryl selected from furyl, thienyl, thiazolyl and oxazolyl, wherein said aryl and heteroaryl groups may optionally be substituted with one or more substituents independently selected from chloro, bromo, nitro, trifluoromethyl, (C1–C6)alkyl, (C1–C6)alkoxy, —S-(C1–C6)alkyl, —SO-(C1–C6)alkyl and —SO2-(C1–C6)alkyl;

R2k and R3k are independently selected from hydrogen, (C1–C6)alkyl, phenyl and phenyl-(C1–C4)alkyl, wherein said phenyl and the phenyl moiety of said phenyl-(C1–C4)alkyl may optionally be substituted with one or more substituents independently selected from (C1–C6)alkyl, (C1–C6)alkoxy, chloro, bromo and trifluoromethyl;

or R2k and R3k form, together with the nitrogen to which they are attached, a cyclic group selected from azetidino, pyrrolidino, piperidino, piperazino and morpholino, wherein said cyclic group may optionally be substituted with from zero to two substituents, independently selected from (C1–C6)alkyl, —CONH2, —SO2NH2, N-(C1–C4)alkylsulfamoyl, N,N-di-(C1–C4)alkylsulfamoyl, (C1–C6)alkoxycarbonyl, N,N-di-(C1–C4)alkylcarbamoyl, N-(C1–C4)alkylcarbamoyl, N-phenylcarbamoyl, (C1–C6)alkylcarbonyl, phenylcarbonyl, (C1–C6) alkylsulfonyl, (C1–C6)alkylsulfinyl, phenylsulfonyl, heteroarylsulfonyl and heteroarylcarbonyl, wherein the heteroaryl moieties of said heteroarylcarbonyl and heteroarylsulfonyl are selected form furyl, thienyl, thiazolyl, and oxazolyl, and wherein the phenyl moieties of said phenylcarbonyl, N-phenylcarbamoyl, phenylcarbonyl and phenylsulfonyl may optionally be substituted with one or more substituents independently selected from (C1–C4)alkyl, (C1–C4)alkoxy, chloro, bromo, nitro, amino, cyano and trifluoromethyl;

R4k is hydrogen, chloro, bromo, cyano, trifluoromethyl, amino, (C1–C6)alkyl, (C1–C6)hydroxyalkyl, (C1–C6)alkoxy, phenyl, naphthyl or furyl, wherein said phenyl, naphthyl and furyl may optionally be substituted with one or more substituents independently selected from chloro bromo, trifluoromethyl, (C1–C6)alkyl, (C1–C6)alkoxy, —S-(C1–C6)alkyl, —SO-(C1–C6)alkyl, —SO2-(C1–C6)alkyl and hydroxy; and R5k is hydrogen, (C1–C6)alkyl, (C1–C6)alkoxy, trifluoromethyl, (C1–C6)hydroxyalkyl, —S-(C1–C6)alkyl, —SO-(C1–C6)alkyl, —SO2-(C1–C6)alkyl, phenyl or furyl, wherein said phenyl and furyl may optionally be substituted with one or more substituents independently selected from chloro, bromo, trifluoromethyl, (C1–C6)alkyl, (C1–C6)alkoxy, —SO-(C1–C6)alkyl, —SO2-(C1–C6)alkyl and hydroxy, are useful for an inhibitor of sorbitol dehydrogenase, and also for lowering the level of fructose.

COMPARISON BETWEEN THE RELATED ARTS AND THE PRESENT INVENTION

Pyridylpyrimidine derivatives of the formula (G), (H) and (J) and (K) described above as related arts, are disclosed as antifungal agent, anti-allergy agent, intermediate of antifungal agent, and anti-diabetes agent and/or its complications, respectively. But, the facts do not suggest that the compounds of the present invention possess inhibitory activity on cGMP-PDE and/or inhibitory activity on TXA2 synthesis. The purposes of those inventions and that of the present invention are different from each other.

On the other hand, from the view point of chemical structure, compounds of formula (G), (H) and (J) all are aminopyrimidine which are substituted by pyridine, But, in the formula (G), disclosure of the substituents corresponding to R3 of the present invention is not specific for hydrogen, methyl, propyl, isopropyl, halogen and benzyl, which are disclosed specifically.

In the formula (H), the description of the substituent corresponding to R3 of the present invention is hydrogen and alkyl, but, only hydrogen is synthesized concretely.

And the compounds of formula (G) have dicarboxylic acid as necessary factor. So from the view point of chemical structure, the compounds of formula (G) and the compounds of the present invention are different.

In the formula (K), disclosure about substituents on the pyrimidine ring corresponding to R1, R2 and R3 of the present invention are not specific but for only 4-piperidinylpyrimidines, which are disclosed specifically. These compounds are R4k and R5k are hydrogen, R1 k is methyl or hydroxymethyl, and R2k and R3k are taken together piperidine ring in the formula (K). These compounds are outside of our invention.

PURPOSE OF THE INVENTION

Energetic investigation has been carried out in order to discover compounds having inhibitory activities on cGMP-PDE or additionally TXA2 synthetase, and as a result, the present inventors have found the compound of formula (I) of the present invention.

SUMMARY OF THE INVENTION

The present invention is related to:

(i) A 4-aminopyrimidine derivative of the formula (I):

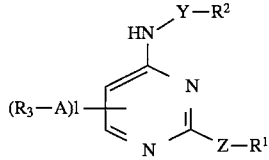

wherein A is a bond, C1-4 alkylene or C1-4 oxyalkylene;

Y is a bond, C1-4 alkylene, C1-4 alkyleneoxy, C1-4 alkoxyphenylene or phenyl(C1-4)alkylene;

Z is a bond or vinylene;

R1 is 4-15 membered heterocyclic ring containing one or two nitrogen atom;

R2 is (i) 4-15 membered heterocyclic ring containing one or two nitrogen, one or two of oxygen or one sulfur atom,
(ii) C4-5 carbocyclic ring,
(iii) C1-4 alkoxy,
(iv) hydroxy(C1-4 alkoxy) or
(v) hydroxy;

R3 is (i) 4-15 membered heterocyclic ring containing one or two nitrogen, one oxygen, one sulfur, or one nitrogen and one sulfur atom,
(ii) C4-15 carbocyclic ring,
(iii) a group of formula:

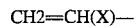

wherein X is halogen.
(iv) hydrogen.

I is 1 or 2.

With the proviso that: the ring represented by R1 may be substituted by one or two of C1-4 alkyl, C1-4 alkoxy, halogen, trifluoromethyl or nitro. The ring represented by R2 may be substituted by one or two of C1-4 alkyl, C1-4 alkoxy, halogen, trifluoromethyl, nitro or a group of formula:

wherein R10 is hydrogen or C1-4 alkyl.

The ring represented by R3 may be substituted by one or two of C1-4 alkyl, C1-4 alkoxy, halogen, trifluoromethyl, nitro, cyano, ethynyl or a group of formula:

wherein R7 and R8 is independently hydrogen or C1-4 alkyl.

With the proviso that, R2 is not hydroxy when Y is a bond; R1 is not bonded through its nitrogen atom when Z is vinylene.

And compounds of the following formula:

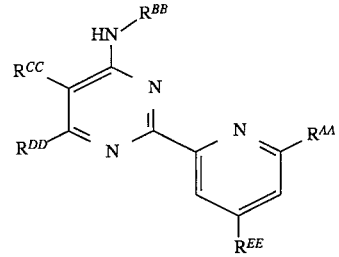

wherein RAA is methyl or n-propyl;

RBB is cyclopentyl, cyclohexyl, 2-hydroxyethyl, methoxyethyl, 2-(1-piperidinyl)ethyl, or phenyl or benzyl which may be substituted by 1 or 2 of methyl, methoxy, chloro, nitro, trifluoromethyl;

RCC is hydrogen or methyl;

RDD is methyl or n-propyl, isopropyl or benzyl;

REE is hydrogen or methyl.

and a compound of formula:

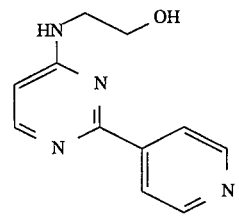

are not included.

and pharmaceutically acceptable acid addition salts thereof and pharmaceutically acceptable salts thereof,
(ii) processes for the preparation thereof,
(iii) inhibitors of cyclic guanosine 3',5'-monophosphate phosphodiesterase, or additionally of thromboxane A2 synthetase containing them, and
(iv) methods of prevention and treatment of mammals, including humans, by administering an effective amount of the compounds of the formula (I), the pharmaceutically acceptable acid addition salts thereof and the pharmaceutically acceptable salts thereof to the patient to be treated.

In the formula (I), 4–15 membered heterocyclic ring containing one or two nitrogen atom represented by R1, R2 and R3 may be saturated or unsaturated one, for example, pyrrole, pyridine, azepine, imidazole, pyrazole, pyrimidine, pyrazine, pyridazine, benzimidazole, quinoline, isoquinoline and partially or fully saturated rings thereof.

As R1, 1-imidazolyl, 1-benzimidazolyl and 3-pyridyl are more preferable.

In the formula (I), 4–15 membered heterocyclic ring containing one or two oxygen atom represented by R2 may be saturated or unsaturated one, for example, furan, pyran, dioxole, dioxine, benzofuran, benzopyran, benzodioxole, benzdioxine and partially or fully saturated rings thereof.

In the formula (I), 4–15 membered heterocyclic rings containing one oxygen atom represented by R3 may be saturated or unsaturated one, for for example, furan, pyran, benzofuran, benzopyran and partially or fully saturated rings thereof.

In the formula (I), 4–15 membered heterocyclic ring containing one sulfur atom represented by R2 and R3 may be saturated or unsaturated one, for example, thiophene, thioine (thiopyran), benzothiophene, benzothione (benzothiopyran) and partially or fully saturated rings thereof.

In the formula (I), 4–15 membered heterocyclic rings containing one nitrogen atom and one sulfur atom represented by R3 may be saturated or unsaturated one, for example, thiazole, isothiazole, thiazine, benzothiazole, benzoisothiazole, benzothiazine and partially or fully saturated rings thereof.

In the formula (I), 4–15 membered carbocyclic rings represented by R2 and R3 may be saturated or unsaturated one, for example, cyclopentene, benzene, cycloheptene, indene, naphthalene and partially or fully saturated rings thereof.

In the formula (I), C1–4 alkyl represented by R7, R8, R9 and in R1, R2 and R3 means methyl, ethyl, propyl, butyl and isomers thereof.

In the formula (I), C1–4 alkoxy in R1, R2 and R3 or represented by R2 means methoxy, ethoxy, propyloxy, butoxy and isomers thereof.

In the formula (I), halogen in R1, R2 and R3 means fluorine, chlorine, bromine and iodine.

In the formula (I), alkylene in C1–4 alkylene, C1–4 alkyleneoxy, C1–4 oxyalkylene or phenyl(C1–4)alkylene represented by A and Y means methylene, ethylene, trimethylene, tetramethylene and isomers thereof.

In the formula (I), alkoxy in C1–4 alkoxyphenylene represented by Y means methoxy, ethoxy, propyloxy, butoxy and isomers thereof. Preferred compounds Preferable compounds included in the present invention are the following compounds and example compounds:

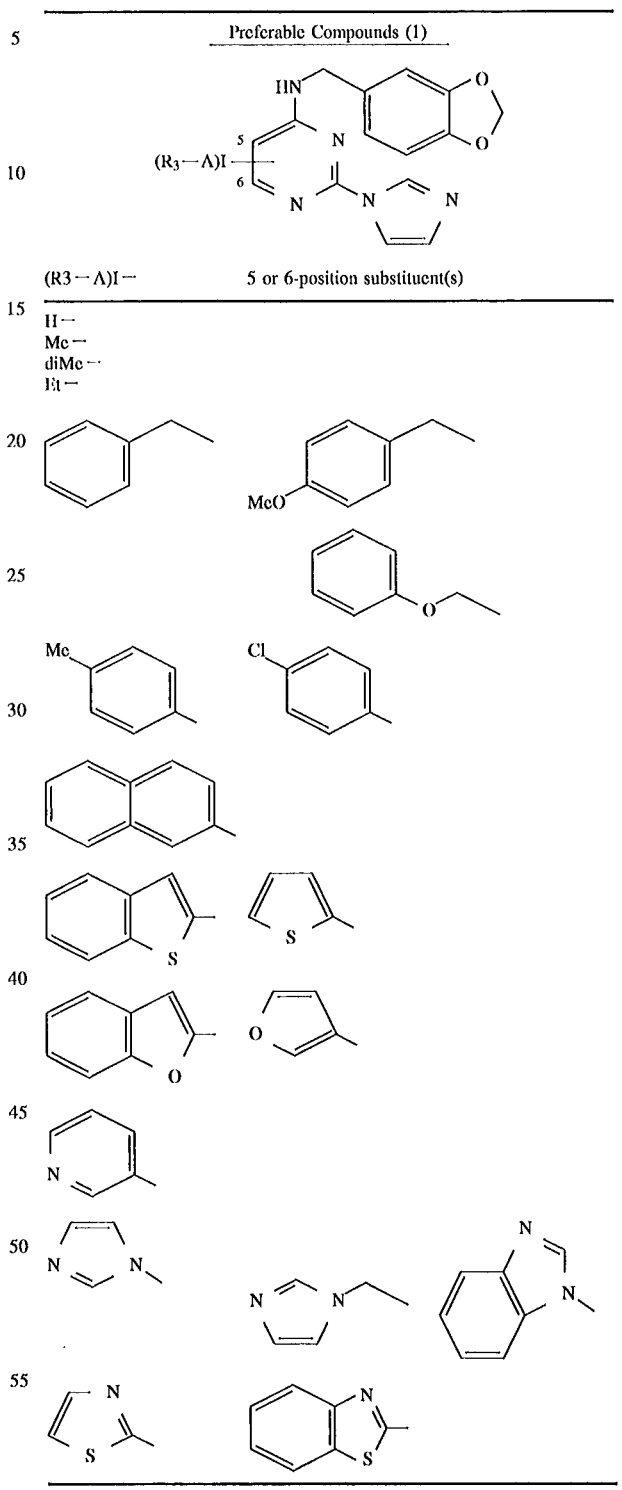

11
-continued
Preferable Compounds (2)
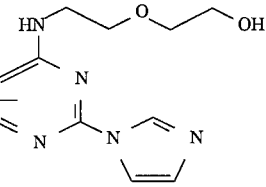
| (R₃—A)l— | 5 or 6-position substituent(s) |
|---|---|
| H— | |
| Me— | |
| diMe— | |
| Et— | |
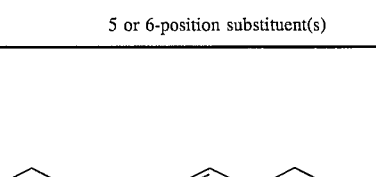 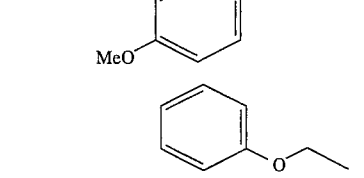
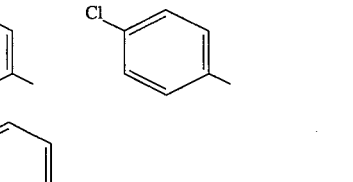
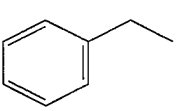 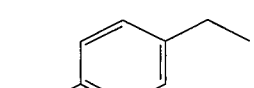
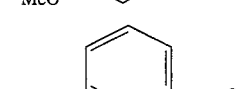
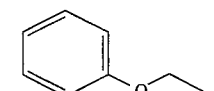 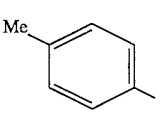
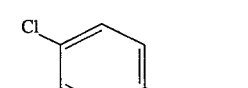 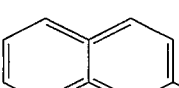
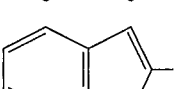
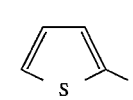 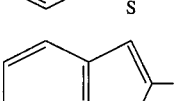 
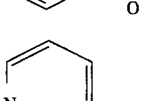 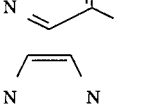
12
-continued
Preferable Compounds (3)
| (R₃—A)l— | 5 or 6-position substituent(s) |
|---|---|
| H— | |
| Me— | |
| diMe— | |
| Et— | |
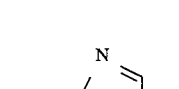 
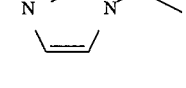

Preferable Compounds (4)

| (R3—A)l— | 5 or 6-position substituent(s) |
|---|---|
| H— | |
| Me— | |
| diMe— | |
| Et— | |

Preferable Compounds (5)

| (R3—A)l— | 5 or 6-position substituent(s) |
|---|---|
| H— | |
| Me— | |
| diMe— | |
| Et— | |

-continued
Preferable Compounds (6)
| (R3—A)l— | 5 or 6-position substituent(s) |
|---|---|
H—
Me—
diMe—
Et—
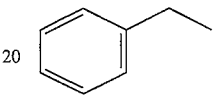 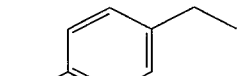
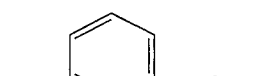
 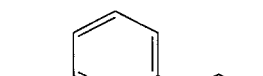
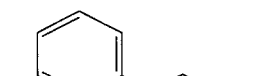
 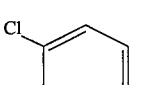
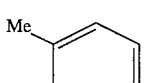 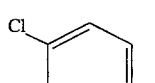
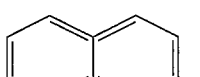  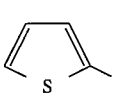
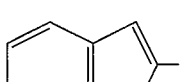 
-continued
Preferable Compounds (7)
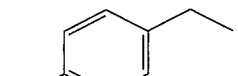
| (R3—A)l— | 5 or 6-position substituent(s) |
|---|---|
H—
Me—
diMe—
Et—
 
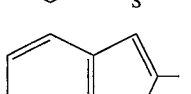
 
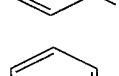
 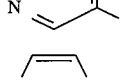
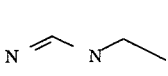 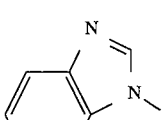
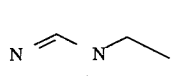
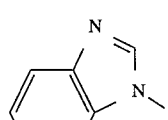  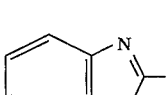
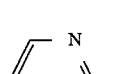 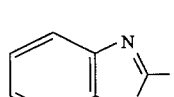

Preferable Compounds (8)

| (R₃—A)l— | 5 or 6-position substituent(s) |
|---|---|
| H— | |
| Me— | |
| diMe— | |
| Et— | |

Preferable Compounds (9)

| (R₃—A)l— | 5 or 6-position substituent(s) |
|---|---|
| H— | |
| Me— | |
| diMe— | |
| Et— | |

-continued

Preferable Compounds (10)

| (R₃—A)I— | 5 or 6-position substituent(s) |
|---|---|
| H— | |
| Me— | |
| diMe— | |
| Et— | |

(phenethyl); (4-methoxyphenethyl); (4-ethoxyphenoxy); (4-methylphenyl); (4-chlorophenyl); (2-naphthyl); (benzothiophen-2-yl); (thiophen-2-yl); (benzofuran-2-yl); (furan-3-yl); (pyridin-3-yl); (imidazol-1-yl); (1-ethylimidazol-yl); (benzimidazol-1-yl); (thiazol-2-yl); (benzothiazol-2-yl)

Preferable Compounds (11)

| (R₃—A)I— | 5 or 6-position substituent(s) |
|---|---|
| H— | |
| Me— | |
| diMe— | |
| Et— | |

(phenethyl); (4-methoxyphenethyl); (4-ethoxyphenoxy); (4-methylphenyl); (4-chlorophenyl); (2-naphthyl); (benzothiophen-2-yl); (thiophen-2-yl); (benzofuran-2-yl); (furan-3-yl); (pyridin-3-yl); (imidazol-1-yl); (1-ethylimidazol-yl); (benzimidazol-1-yl); (thiazol-2-yl); (benzothiazol-2-yl)

-continued
Preferable Compounds (12)
Preferable Compounds (13)
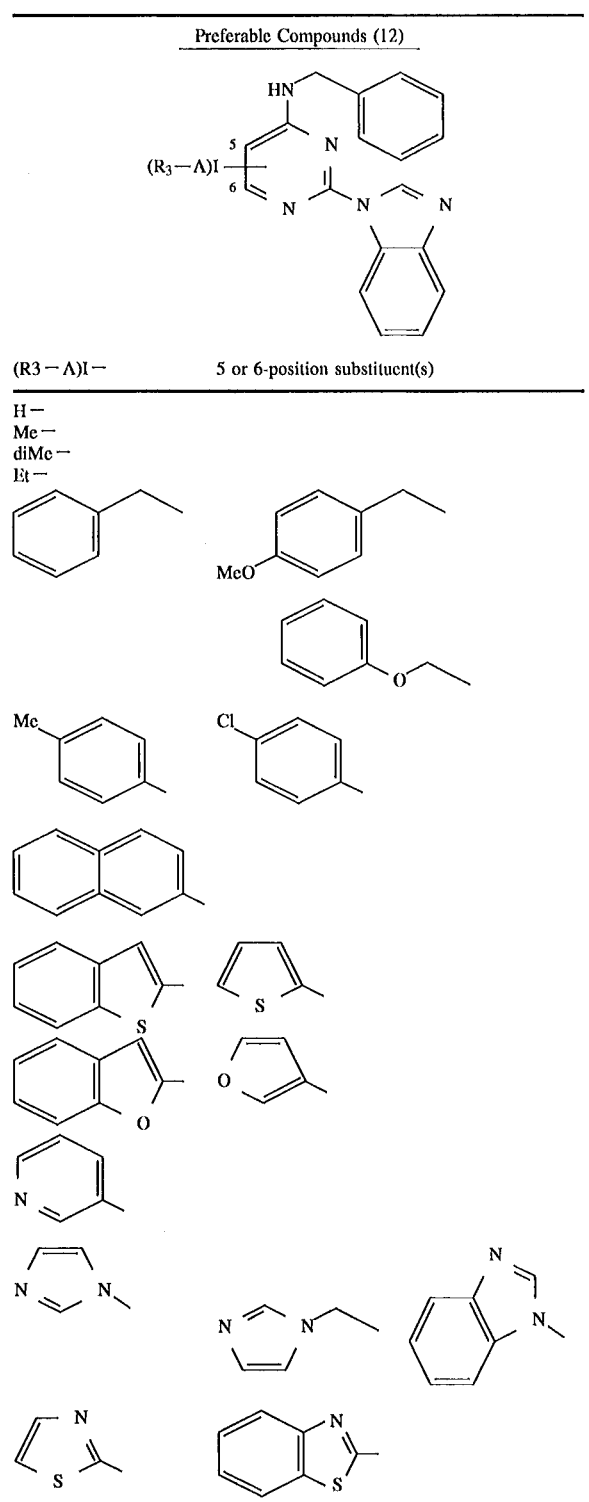
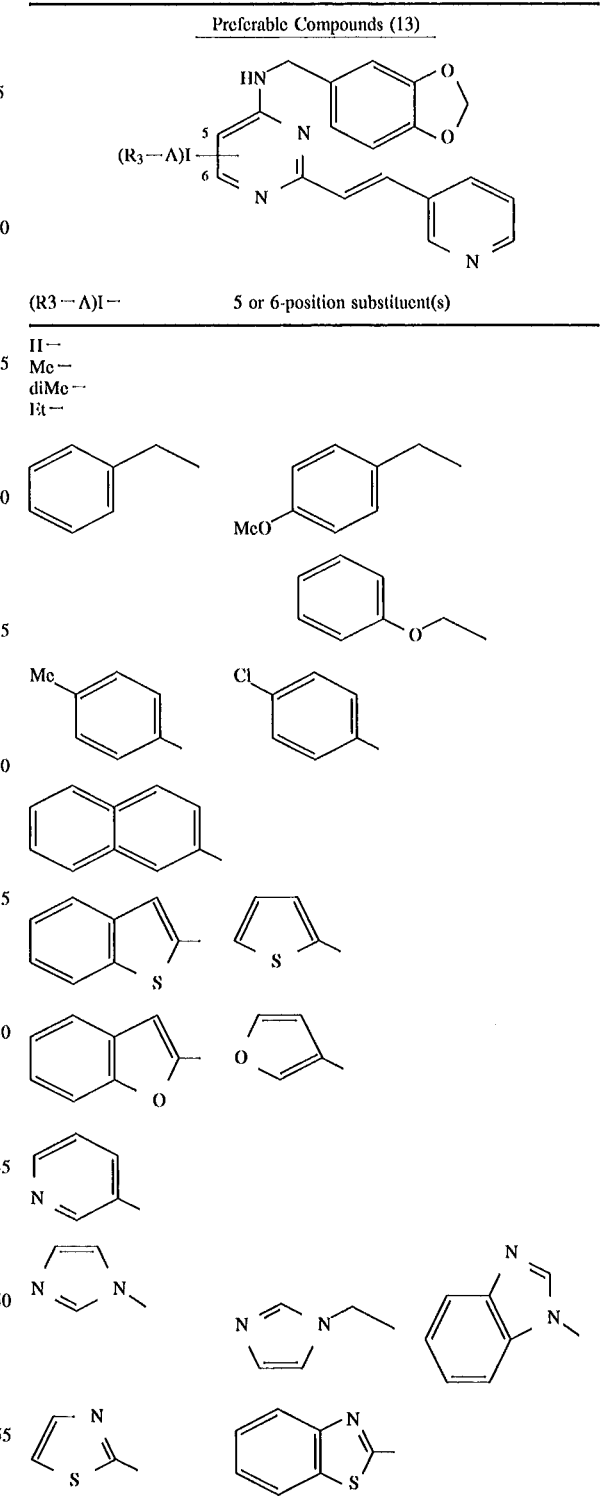

Preferable Compounds (14)
| (R₃—A)l— | 5 or 6-position substituent(s) |
|---|---|
| H— | |
| Me— | |
| diMe— | |
| Et— | |
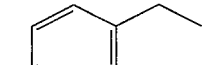 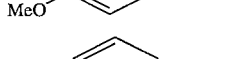
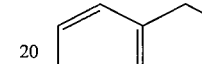
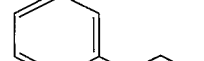 
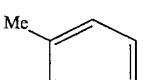
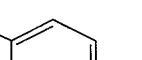 
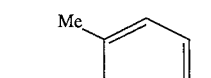 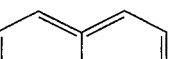
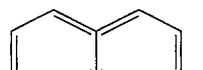
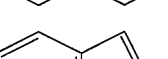  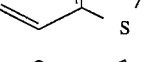
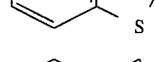 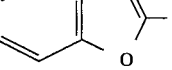
Preferable Compounds (15)
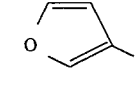
| (R₃—A)l— | 5 or 6-position substituent(s) |
|---|---|
| H— | |
| Me— | |
| diMe— | |
| Et— | |
 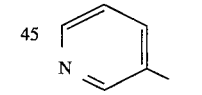
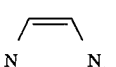
 
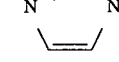
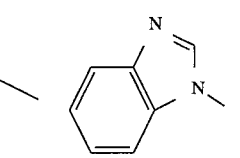 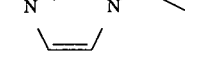
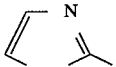
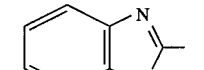 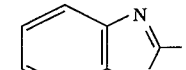
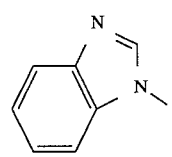

Preferable Compounds (16)

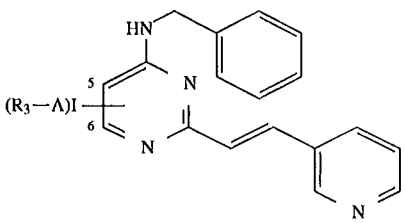

| (R3—A)l— | 5 or 6-position substituent(s) |
|---|---|

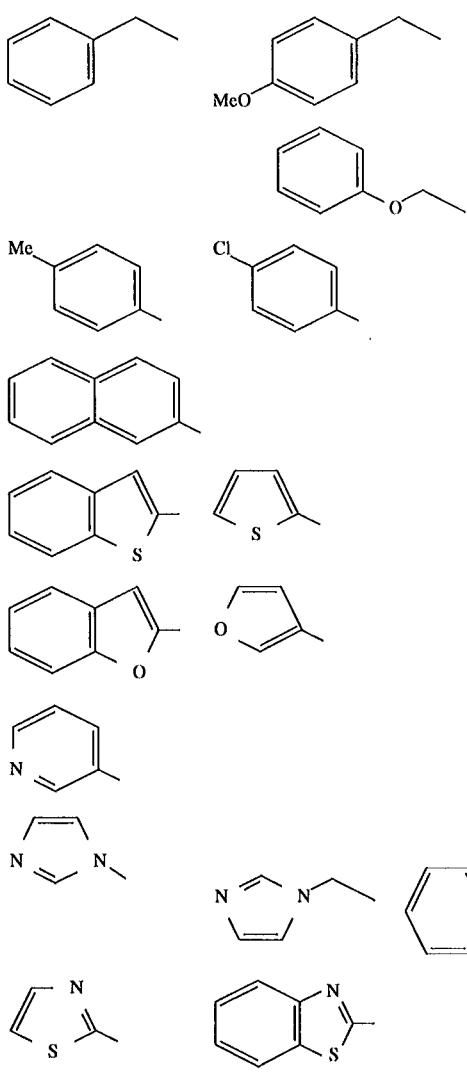

Salts and Acid addition salts

The compounds of the formula (I), if desired, may be convened into acid addition salts by known methods. Preferably, acid addition salts are non-toxic and water-soluble. The suitable acid addition salts are, for example, salts of an inorganic acid such as hydrochloric acid, hydrobromic acid, hydroiodic acid, sulfuric acid, phosphoric acid, nitric acid, or an organic acid such as acetic acid, lactic acid, tartaric acid, benzoic acid, citric acid, methanesulfonic acid, ethane- sulfonic acid, benzenesulfonic acid, toluenesulfonic acid, isethionic acid, glucuronic acid and gluconic acid. Preferable salt is hydrochloride.

The compounds of the formula (I), if desired, may be convened into salts by known methods. Preferable, salts are non-toxic salts and water-soluble. The suitable salts are salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, phenylmethylamine, phenethylamine, piperidine, monoethanolamine, diethanolamine, tris(hydroxymethyl)methylamine, lysine, arginine, N-methyl-D-glucamine etc.).

Throughout the specification including claims, it may be easily understood by those skilled in the art, that the alkyl, alkoxy, alkylene, alkenylene groups include straight-chained and also branched-chained ones. Accordingly, all isomers produced by the difference in stereo configuration, such as asymmetric carbons are included in the present invention.

Process for the Preparations

Among the compounds of the present invention of the formula (I), compounds wherein Z is a bond and R1 is a heterocyclic ring bonded to the pyrimidine ring through its nitrogen atom of formula (IA):

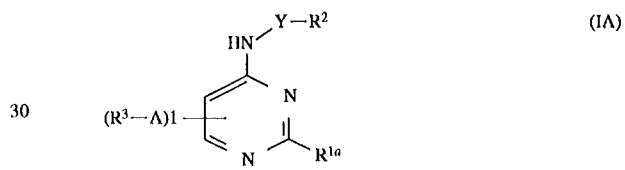

wherein R1a is as defined for R1 wherein its nitrogen atom is bonded to the pyrimidine ring and the other symbols are the same meaning as hereinbefore defined.

May be prepared by reacting a compound of formula (II):

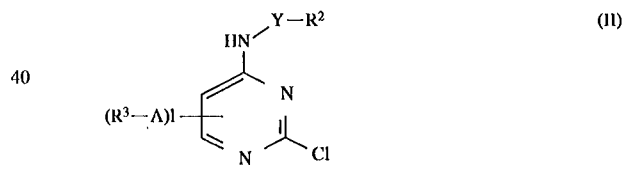

wherein all symbols are the same meaning as hereinbefore defined, and a compound of formula (III):

wherein R1a is the same meaning as hereinbefore defined.

The reaction is known, for example, it may be carried out in a proper organic solvent such as a lower alkanol (e.g. ethanol), tetrahydrofuran or mixture thereof, at a temperature of ambient to reflux, for several hours to several days, at a presence or absence of a base such as triethylamine.

Among the compounds of the present invention of the formula (I), compounds wherein Z is a bond and R1 is a heterocyclic ring bonded to the pyrimidine ring through its carbon atom of the formula (IB):

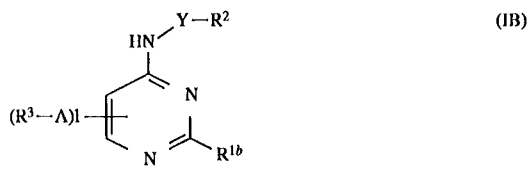

wherein R1b is as defined for R1 wherein its carbon atom is bonded to the pyrimidine ring and the other symbols are the same meaning as hereinbefore defined.
May be prepared by reacting a compound of formula (VII)

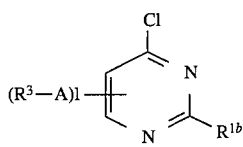                    (VII)

wherein all symbols are the same meaning as hereinbefore defined. and a compound of formula (IV)

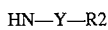                    (IV)

wherein all symbols are the same meaning as hereinbefore defined.

The reaction is known, for example, it may be carried out in a proper organic solvent such as a lower alkanol (e.g. ethanol), tetrahydrofuran or mixture thereof, at a temperature of ambient to reflux, for several hours to several days, at a presence or absence of a base such as triethylamine.

Among the compounds of the present invention of the formula (I), compounds wherein Z is vinylene and R1 is a heterocyclic ring bonded to the pyrimidine ring through its nitrogen atom of the formula (IC):

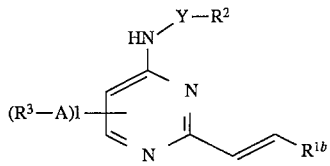                    (IC)

wherein all symbols are the same meaning as hereinbefore defined.
May be prepared by reacting a compound of formula (XIV):

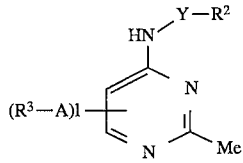                    (XIV)

wherein all symbols are the same meaning as hereinbefore defined. and a compound of formula (XV):

                    (XV)

wherein all symbols are the same meaning as hereinbefore defined.

The reaction is known, for example, it may be carried out in an organic acid such as acetic acid, trichloroacetic acid etc., with refluxing.

The compounds of the formula (II), (VII) and (XIV) may be prepared by a series of reactions depicted in Scheme (A), (B) and (C), respectively. Wherein X1 is halogen, R10 is C1–4 alkyl, R3a is the same meaning as R3 provided that ethynyl or CH2=C(X)— is protected form, i.e. trialkylsillyl and the other symbols are the same meaning as hereinbefore defined.

Scheme A

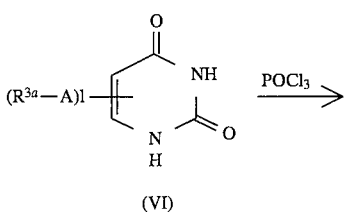

(VI)

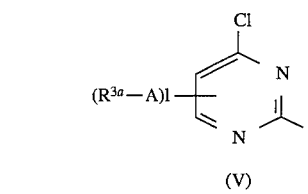

(V)

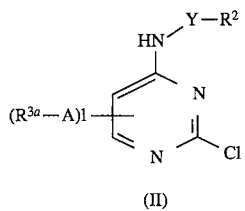

(II)

Scheme B

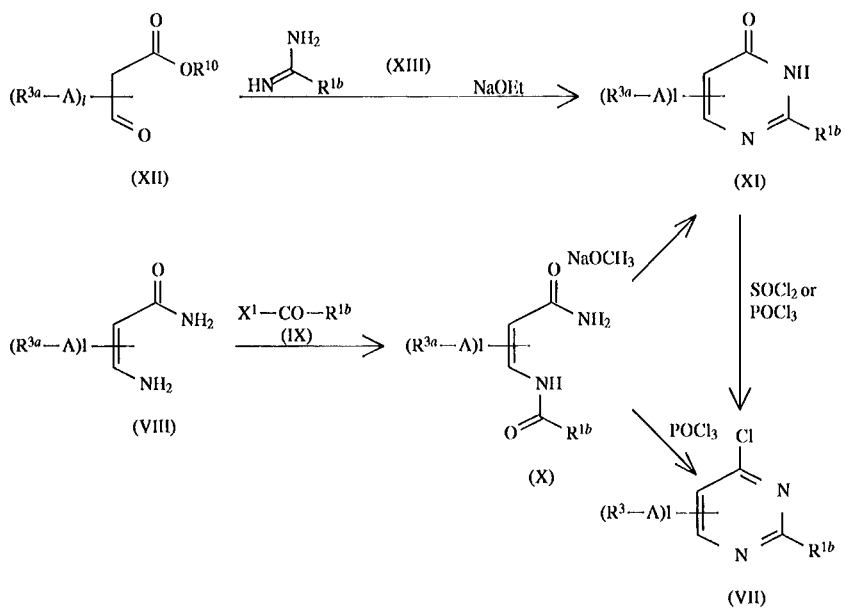

Scheme C

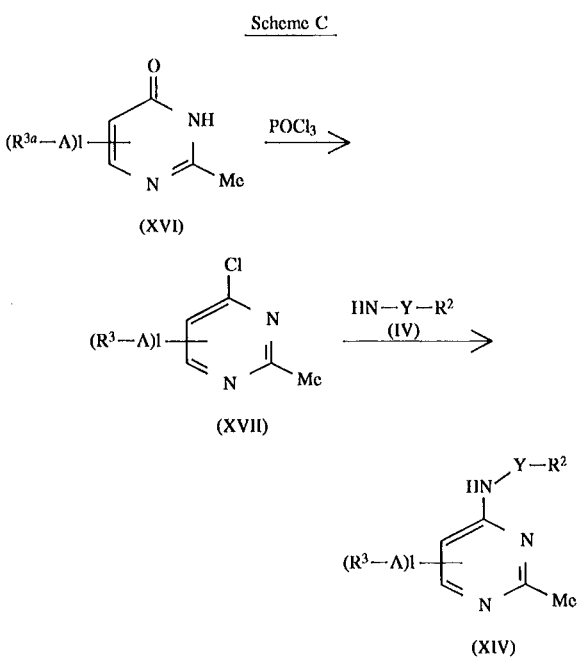

Among the compounds of the formula (I), compounds wherein carboxy group are contained in R2 may be prepared from compounds wherein alkoxycarbonyl group are contained in R2 by hydrolysis.

Hydrolysis is known, for example, it may be carried out in a water miscible organic solvent (ethanol, methanol, tetrahydrofuran etc.) with an aqueous solution of alkali (sodium hydroxide, potassium hydroxide etc.) at 10° C. to 80° C.

The compounds of the formula (IB) may also be prepared by a compound of the formula (II)

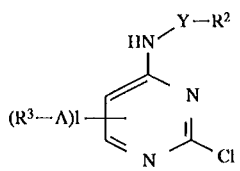

wherein all symbols are the same meaning as hereinbefore defined. and a compound of formula (XX)

Et2B—R1b (XX)

wherein all symbols are the same meaning as hereinbefore defined.

The reaction is known, it may be carried out, for example, in an inert organic solvent (dimethoxyethane, tetrahydrofuran etc.) using an aqueous solution of alkali (sodium hydrocarbonate, sodium hydroxide, potassium hydroxide etc.) and a catalyst (tetrakis(triphenylphosphine)palladium etc. with refluxing.

The compounds of formula (III), (IV), (VI), (VIII), (IX), (XII), (XIII), (XV), (XVI) and (XX) are known per se or prepared by known method per se.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction or after a series of reactions.

Effect

The compounds of the formula (I), pharmaceutically acceptable acid addition salts thereof, pharmaceutically acceptable salts thereof, or hydrates thereof, of the present invention have an inhibitory effect on cGMP-PDE, or additionally on TXA2 synthetase, and are, therefore, useful for the prevention and/or treatment of not only diseases induced by enhancement of the metabolism of cGMP, such as hypertension, heart failure, myocardial infarction, angina, atherosclerosis, cardiac edema, renal insufficiency, nephrotic edema, hepatic edema, asthma, bronchitis, dementia, immunodeficiency, but also diseases induced by enhancement of the synthesis of TXA2 such as inflammation, thrombosis, cerebral apoplexy, asthma, cardiostenosis, cerebral infarction etc., in mammals, especially in humans.

Especially, it is very useful for the prevention and/or treatment of heart failure, angina pectoris, pulmonary hypertension, various kinds of renal diseases, hypouresis induced by heart failure.

The inhibitory effect on cGMP-PDE, of the compounds of the present invention were confirmed by screening tests as described below.

(1) Inhibitory effect on cGMP-PDE
Method

PDE IC was isolated from human platelets according to standard methods previously described in Lugnier, C. et al., Biochem. Pharmacol. 35: 1743, 1986 (incorporated in its entirety by reference). Typically, connective tissue and adventitia were removed and 1–2 units of platelets were suspended in 10 volumes of buffer A (20 mM Tris-HCl, pH 7.5, containing 2 mM magnesium acetate, 1 mM dithiothreitol, and 5 mM Na2EDTA) using a Brinkman polytron. The proteinase inhibitors leupeptin, pepstatin A, and phenylmethyl-sulfonyl fluoride (PMSF) were also included in this buffer (final concentration of 100 nM each). The homogenate was centrifuged at 100,000 g for 60 minutes. The supernatant was then removed and filtered through four layers of cheesecloth. The supernatant was applied to a DEAE-trisacryl M column. The column was washed with several bed volumes of buffer B (20 mM Tris-HCl, pH 7.5, containing 2 mM magnesium acetate, 1 mM dithiothreitol, and proteinase inhibitors) and eluted by two successive linear NaCl gradients (0.05–0.15M, 300 ml total; 0.15–0.40M, 200 ml total). Five milliliter fractions were collected and assayed for cyclic GMP PDE activity.

Phosphodiesterase activity was measured, as described by Thompson, et al., Adv. Cyclic Nucleotide Res. 10: 69, 1979 (incorporated in its entirety by reference), in a reaction medium containing 40 mM Tris-HCl (pH 8.0), 5 mM MgCl2, and 1 mM dithiothreitol. The concentration of substrate (3H-cGMP) was 0.2 μM. Compounds of the present invention were dissolved in dimethyl sulfoxide (DMSO) at a final concentration of 2.5%. This concentration of DMSO inhibited enzyme activity by approximately 10%. The IC50 values (concentration that produced 50% inhibition of substrate hydrolysis) for the compounds examined were determined from concentration-response curves in which concentrations typically ranged from $10^{-8}$ to $10^{-3}$M for the less potent inhibitors (half-log increments).

Result

The result is shown in Table 1 below.

TABLE 1

| Inhibitory activity on cGMP-PDE | |
|---|---|
| Compounds Example No. | Inhibitory activity IC50, (μM) |
| 1 | 21.0 |
| 1(a) | 38.0 |
| 1(c) | 2.5 |
| 1(d) | 1.0 |
| 1(e) | 18.0 |
| 1(f) | 3.65 |
| 1(g) | 3.8 |
| 1(h) | 0.7 |

TABLE 1-continued

| Inhibitory activity on cGMP-PDE | |
|---|---|
| Compounds Example No. | Inhibitory activity IC50, (μM) |
| 1(i) | 3.5 |
| 1(j) | 0.78 |
| 1(k) | 0.76 |
| 1(l) | 35.0 |
| 1(m) | 1.25 |
| 1(o) | 0.12 |
| 1(p) | 0.025 |
| 1(q) | 12.5 |
| 1(r) | 0.35 |
| 1(t) | 0.23 |
| 1(u) | 1.0 |
| 1(v) | 0.31 |
| 1(w) | 2.0 |
| 1(x) | 6.0 |
| 1(y) | 2.7 |
| 1(z) | 0.061 |
| 1(bb) | 0.014 |

(2) Inhibitory effect on TXA2 synthetase
Method

Male Wistar rats were starved overnight. 500 μL of heparinized (10 U/mL) whole blood was collected from abdominal aorta using polyethylene syringe (needle: 22 or 26 G). The blood freshly drawn from animal was preincubated with 5 μL Of test compound (concentration 10 μM) at 37° C. Five minutes later, 2.5 μL of 6 mM of Ca ionophore A23187 (final concentration of 30 mM) was added into tube, and incubation mixture was further incubated for 15 min. The reaction was terminated by centrifugation of tubes at 12,000 rpm for 2 min. TXB2 content in the supernatant was determined by EIA as follows.

1 mL of 0.5M glycine-HCl buffer (pH 3.2) was added to 100 μL of sample. The samples were mixed well and centrifuged at 1,700 G for 10 min. at 4° C. The extracted supernatant was applied to a SEP-PAK (registered Trade Mark) C18 cartridge (Waters Assoc.). After washing with 10 mL of distilled water followed by 10 mL each of 15% ethanol and petroleum ether, the sample was eluted with 3 mL of ethyl acetate. The ethyl acetate fraction was evaporated to dryness under gentle N2 stream and the residue was dissolved in EIA buffer (final volume of 1 mL) following the addition of 300 mL of 0.01M NaHCO3-NaOH buffer (pH 10.0). EIA for TXB2 was carried out according to a legend attached to the kit (Chyman Chemical Co., inc.) and calculated inhibition percent. Overall recovery of TXB2 in this extraction procedure was 90%.

Result

TABLE 2

| Inhibitory activity on TXA2 synthetase | |
|---|---|
| Compounds Example No. | Inhibitory activity Inhibition (%) at 10 μM |
| 1(h) | 99 |
| 1(j) | 94 |
| 1(l) | 63 |
| 1(n) | 90 |
| 1(o) | 65 |
| 1(p) | 90 |
| 1(q) | 100 |
| 1(t) | 100 |
| 1(u) | 96 |
| 1(v) | 100 |
| 1(w) | 83 |

TABLE 2-continued

| Compounds Example No. | Inhibitory activity Inhibition (%) at 10 μM |
|---|---|
| 1(x) | 87 |
| 1(y) | 89 |
| 1(bb) | 90 |
| 2 | 75 |

Toxicity

On the other hand, it was confirmed that the acute toxicity of the compound of the present invention is very weak. Therefore, the compounds of the present invention may be considered to be sufficiently safe and suitable for pharmaceutical use.

Application for Pharmaceuticals

For the purpose above described, the compounds, of the formula (I), of the present invention, pharmaceutically acceptable salts and acid addition salts thereof and hydrates thereof may be normally administered systemically or partially, usually by oral or parenteral administration.

The doses to be administered are determined depending upon age, body weight, symptom, the desired therapeutic effect, the route of administration, and the duration of the treatment etc. In the human adult, the doses per person are generally between 1 mg and 1000 mg, by oral administration, up to several times per day, and between 1 mg and 100 mg, by parenteral administration up to several times per day, or continuous administration between 1 and 24 hrs. per day intravenously.

As mentioned above, the doses to be used depend upon various conditions. Therefore, there are cases in which doses lower than or greater than the ranges specified above may be used.

Administration of the compounds of the present invention, may be as solid compositions, liquid compositions or other compositions for oral administration, as injections, liniments or suppositories etc. for parenteral administration.

Solid compositions for oral administration include compressed tablets, pills, capsules, dispersible powders, and granules. Capsules include hard capsules and soft capsules.

In such compositions, one or more of the active compound(s) is or are, admixed with at least one inert diluent (such as lactose, mannitol, glucose, hydroxypropyl cellulose, micro crystalline cellulose, starch, polyvinylpyrrolidone, magnesium metasilicate aluminate etc.) The compositions may also comprise, as is normal practice, additional substances other than inert diluents: e.g. lubricating agents (such as magnesium stearate etc.), disintegrating agents (such as cellulose calcium glycolate etc.), stabilizing agents (such as lactose etc.), and assisting agents for dissolving (such as glutamic acid, aspartic acid etc.).

The tablets or pills may, if desired, be coated with film of gastric or enteric material (such as sugar, gelatin, hydroxypropyl cellulose or hydroxypropylmethyl cellulose phthalate etc.), or be coated with two or more films. And further, coating may include containment within capsules of absorbable materials such as gelatin.

Liquid compositions for oral administration include pharmaceutically-acceptable solutions, emulsions, suspensions, syrups and elixirs.

In such compositions, one or more of the active compound(s) is or are comprised in inert diluent(s) commonly used in the art (purified water, ethanol etc.).

Besides inert diluents, such compositions may also comprise adjuvants (such as wetting agents, suspending agents etc.), sweetening agents, flavoring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.)

For preparation of such spray compositions, for example, the method described in the U.S. Pat. No. 2,868,691 or 3,095,355 (each incorporated herein by reference) may be used.

Injections for parenteral administration include sterile aqueous or non-aqueous solutions, suspensions and emulsions. In such compositions, one more of active compound(s) is or are admixed with at least one of inert aqueous diluent(s) (distilled water for injection, physiological salt solution etc.) or inert non-aqueous diluent(s)(propylene glycol, polyethylene glycol, olive oil, ethanol, POLYSOLBATE80 (registered trade mark) etc.).

Injections may comprise additional other than inert diluents: e.g. preserving agents, wetting agents, emulsifying agents, dispersing agents, stabilizing agent (lactose etc.), assisting agents such as assisting agents for dissolving (glutamic acid, aspartic acid etc.).

They may be sterilized for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for parenteral administration include liquids for external use, and endermic liniments (ointment etc.), suppositories and pessaries which comprise one or more of the active compound(s) and may be prepared by known methods.

Reference example and Examples

The following Reference examples and examples are intended to illustrate, but not limit, the present invention. In Reference examples and examples, "mp" shows "melting point". Unless otherwise specified, "NMR" was measured in dimethylsulphoxide-d6 and "IR" was measured by the KBr tablet method, respectively.

Reference example 1

2,4-Dichloro-5-(3-methoxyphenyl)methylpyrimidine

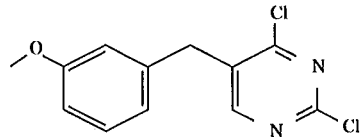

N,N-dimethylaniline (1 ml) was added to a mixture of 5-(3-methoxyphenyl)methyl-1,2,3,4-tetrahydropyrimidin-2, 4-dione (6.2 g)in phosphorous oxychloride (80 ml). The mixture was refluxed overnight. After cooling, the mixture was poured into a mixture of ice and water. The mixture was extracted with chloroform. The extract was dried and evaporated. The residue was purified by column chromatography on silica gel to give the title compound (5.3 g) having the following physical data: NMR (CDCl3): δ3.79 (s, 3H), 4.02 (s, 2H), 6.72 (m, 3H), 7.26 (m, 2H), 8.31 (m, 1H).

Reference example 2

2-Chloro-4-[2-(2-hydroxyethoxy)ethyl]amino-5-(3-methoxyphenyl)methyl-pyrimidine

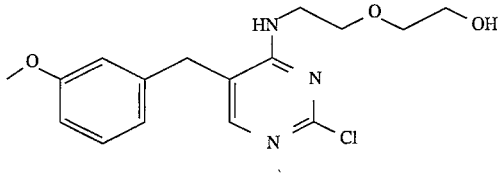

2-(2-Aminoethoxy)ethanol (0.59 g) and triethylamine (20.5 ml) were added to a solution of the compound prepared in reference example 1 (1.0 g) in ethanol (50 ml). The mixture was refluxed overnight. The mixture was evaporated. The residue was taken up in chloroform and water. The oily layer was dried and evaporated to give the title compound (1.3 g).

EXAMPLE 1

2-(1-Imidazolyl)-4-[2-(2–hydroxyethoxy)ethyl]-amino-5-(3-methoxy phenyl)methylpyrimidine and its dihydrochloride

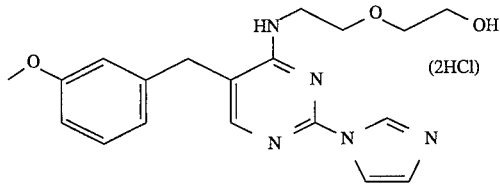

A mixture of the compound prepared in reference example 2 (1.3 g) and imidazole (2.7 g) in ethanol (5 ml) was heated to 140° C. with removal of ethanol by distillation. After heating 2.5 hours, the mixture was allowed to cool to room temperature. The resulting material was taken up in water. The solution was extracted with chloroform. The extract was dried and evaporated. The residue was purified by column chromatography on silica gel to give the title compound (free base; 0.7 g) having the following physical data: NMR (CDCl3): δ3.66 (m, 8H), 3.78 (s, 3H), 6.78 (m, 3H), 7.28 (t, 1H), 7.68 (s, 1H), 7.82 (s, 1H), 7.96 (s, 1H), 8.54 (s, 1H).

HCl in methanol (0.5 ml; 10%) was added to a mixture of the free base (0.7 g) obtained above in methanol (5 ml). The solution was evaporated. The resulting material was collected and dried in vacuo to give the title compound (HCl salt; 0.3 g) having the following physical data:

mp=55°–65° C.; NMR: δ3.44.(m, 3H), 3.60 (m, 6H), 3.79 (s, 3H), 3.87 (s, 2H), 6.90 (m, 3H), 7.22 (t, 1H), 7.66 (t, 1H), 7.84 (s, 1H), 8.01 (s, 1H), 8.31 (s, 1H), 9.86 (s, 1H),

By the same procedure as described in reference examples 1 and 2 and example 1, the following compounds were given.

EXAMPLE 1(a)

2-(1-Imidazolyl)-4-phenylmethylaminopyrimidine and its dihydrochloride

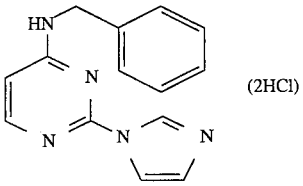

free base
mp=140°–142° C.; NMR (CDCl3): δ4.63 (d, 1H), 5.50 (brs, 1H), 6.24 (d, 1H), 7.11 (s, 1H), 7.36 (m, 5H), 7.82 (s, 1H), 8.12 (d, 1H), 8.54 (s, 1H).
2HCl salt
mp=164° C. (decomposed); NMR:δ4.71 (m, 2H), 6.70 (d, 1H), 7.21–7.50 (m, 5H), 7.86 (s, 1H), 8.18 (d, 1H), 8.33 (s, 1H), 8.83 (m, 1H), 9.93 (s, 1H).

EXAMPLE 1(b)

2-(1-Imidazolyl)-4-(2-methoxyethyl)aminopyrimidine and its dihydrochloride

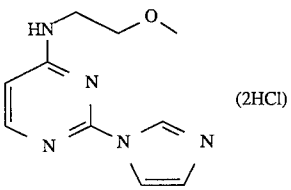

free base
mp=84°–85° C.; NMR (CDCl3): δ3.42 (s, 3H), 3.62 (brs, 4H), 5.72 (br, 1H), 6.26 (d, 1H), 7.13 (s, 1H), 7.83 (s, 1H), 8.12 (d, 1H), 8.55 (s, 1H).
2HCl salt
mp=167° C.; NMR: δ3.29 (s, 3H), 3.52 (m, 2H), 3.64 (m, 2H), 6.68 (d, 1H), 7.86 (s, 1H), 8.13 (d, 1H), 8.34 (s, 1H), 8.42 (m, 1H), 9.93 (s, 1H).

EXAMPLE 1(c)

2-(1-Imidazolyl)-5-ethyl-4-phenylmethylaminopyrimidine and its dihydrochloride

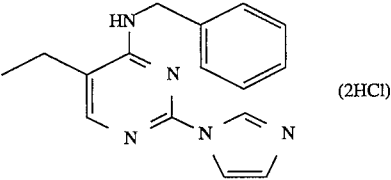

free base
mp=105°–106° C.; NMR: δ1.17 (t, 3H), 2.50 (qd, 2H), 4.67 (d, 2H), 7.02 (s, 1H), 7.13–7.42 (m, 5H), 7.76 (s, 1H), 7.93 (s, 1H), 8.00 (t, 1H), 8.37 (s, 1H).
2HCl salt
mp=207°–209° C.; NMR: δ1.18 (t, 3H), 2.55 (qd, 2H), 4.78 (d, 2H), 7.18–7.35 (m, 3H), 7.43 (d, 2H), 7.84 (s, 1H), 8.05 (s, 1H), 8.27 (s, 1H), 8.42 (t, 1H), 9.88 (s, 1H).

EXAMPLE 1(d)

2-(1-Imidazolyl)-5-phenylmethyl-4-phenylmethylaminopyrimidine and its dihydrochloride

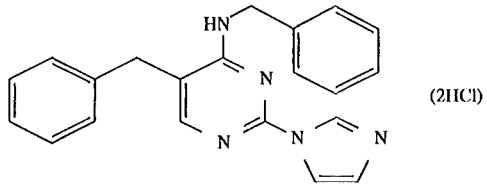

free base mp=167°–169° C.; NMR (CDCl3): δ3.83 (s, 2H), 4.62 (d, 2H), 5.06 (brs, 1H), 6.95–7.40 (m, 11H), 7.80 (s, 1H), 8.01 (s, 1H), 8.52 (s, 1H).

2HCl salt mp=172°–175° C.; NMR: δ3.96 (s, 2H), 4.74 (m, 2H), 7.15–7.40 (m, 10H), 7.78 (s, 1H), 8.06 (s, 1H), 8.24 (s, 1H), 8.28 (m, 1H), 9.75 (s, 1H).

EXAMPLE 1(e)

2-(1-Imidazolyl)-5-methyl-4-phenylmethylaminopyrimidine and its dihydrochloride

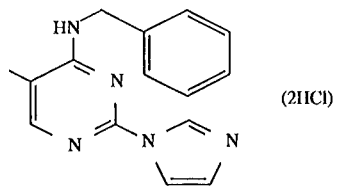

free base mp=155°–158° C.; NMR: δ2.08 (s, 3H), 4.68 (d, 2H), 7.03 (s, 1H), 7.17–7.45 (m, 5H), 7.77 (s, 1H), 7.94 (m, 2H), 8.39 (s. 1H).

2HCl salt mp=200°–205° C.; NMR: δ2.13 (s, 3H), 4.78 (d, 2H), 7.18–7.49 (m, 5H), 7.84 (s, 1H), 8.07 (s, 1H), 8.33 (t, 1H), 9.89 (s, 1H).

EXAMPLE 1(f)

2-(1-Imidazolyl)-5,6-dimethyl-4-phenylmethylaminopyrimidine and its dihydrochloride

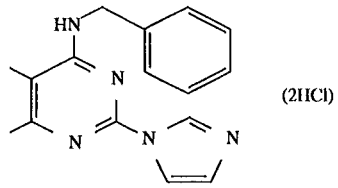

free base mp=194°–196° C.; NMR: δ2.06 (s, 3H), 2.31 (s, 3H), 4.63 (d, 2H), 7.01 (s, 1H), 7.18–7.42 (m, 5H), 7.74 (s, 1H), 7.79 (t, 1H), 8.35 (s, 1H).

2HCl salt mp=175°–240° C.; NMR: δ2.11 (s, 3H), 2.37 (s, 3H), 4.74 (d, 2H), 7.19–7.48 (m, 6H), 7.82 (s, 1H), 8.15 (t, 1H), 8.23 (s, 1H), 9.82 (s, 1H).

EXAMPLE 1(g)

2-(1-Imidazolyl)-5-(3-methoxyphenyl)methyl-4-(2-methoxyethyl)aminopyrimidine and its dihydrochloride

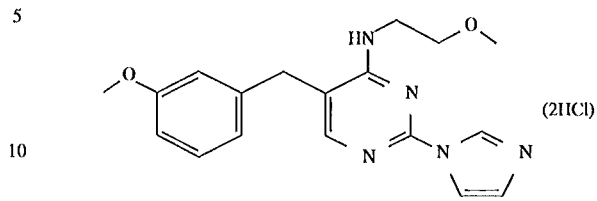

free base mp=111°–113° C.; NMR: δ3.25 (s, 3H), 3.52 (t, 2H), 3.63 (t, 2H), 3.74 (s, 3H), 3.80 (s, 2H), 6.83 (m, 3H), 7.07 (s, 1H), 7.22 (t, 2H), 7.30 (t, 1H), 7.84 (s, 1H), 7.89 (s, 1H), 8.47 (s, 1H).

2HCl salt mp=70°–90° C.; NMR: δ3.25 (s, 3H), 3.52 (t, 2H), 3.69 (t, 2H), 3.74 (s, 3H), 3.88 (s, 2H), 6.88 (m, 3H), 7.23 (t, 1H), 7.72 (t, 1H), 7.84 (s, 1H), 8.02 (s, 1H), 8.32 (s, 1H), 9.88 (s, 1H).

EXAMPLE 1(h)

2-(1-Imidazolyl)-5-(4-methoxyphenyl)methyl-4-[2-(2-hydroxyethoxy)ethyl]aminopyrimidine and its dihydrochloride

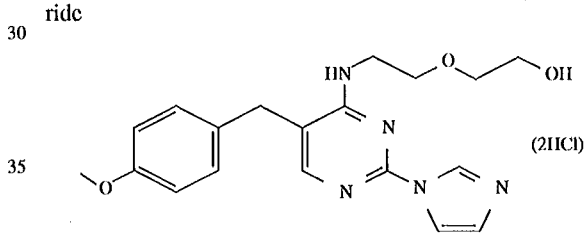

free base mp=91°–93° C.; NMR: δ3.48 (m, 6H), 3.51 (m, 2H), 3.73 (s, 3H), 3.75 (s, 1H), 6.90 (d, 2H), 7.06 (s, 1H), 7.22 (d, 2H), 7.86 (d, 2H), 8.47 (s, 1H).

2HCl salt mp=152°–158° C.; NMR: δ3.45 (m, 4H), 3.60–3.70 (m, 4H), 3.72 (s, 3H), 3.83 (s, 2H), 6.86 (d, 2H), 7.25 (d, 2H), 7.67 (t, 1H), 7.85 (s, 1H), 7.98 (s, 1H), 8.31 (s, 1H), 9.88 (s, 1H).

EXAMPLE 1(i)

2-(1-Imidazolyl)-5-(4-methoxyphenyl)methyl-4-(2-methoxyethyl)aminopyrimidine and its dihydrochloride

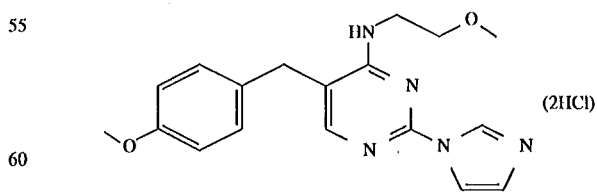

free base mp=125°–127° C.; NMR: δ3.24 (s, 3H), 3.50 (m, 2H), 3.73 (m, 2H), 6.89 (d, 2H), 7.05 (s, 1H), 7.17 (m, 3H), 7.84 (s, 2H), 8.46 (s, 1H).

2HCl salt mp=148°–155° C.; NMR: δ3.24 (s, 3H), 3.51 (t, 2H), 3.68 (t, 2H), 3.72 (s, 3H), 3.81 (s, 2H), 6.86 (d, 2H), 7.20 (d, 2H), 7.78 (t, 1H), 7.84 (s, 1H), 7.96 (s, 1H), 8.31 (s, 1H), 9.86 (s, 1H).

EXAMPLE 1(j)

2-(1-Imidazolyl)-5-(4-methoxyphenyl)methyl-4-phenylmethylaminopyrimidine and its dihydrochloride

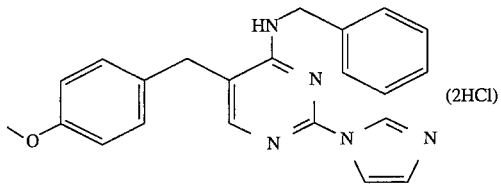

free base
mp=144°–147° C.; NMR: δ3.73 (s, 2H), 3.81 (s, 3H), 4.66 (d, 2H), 6.86 (d, 2H), 7.19 (s, 1H), 7.25 (m, 4H), 7.76 (s, 1H), 7.89 (s, 2H), 8.37 (s, 1H).
2HCl salt
mp=86° C. (decomposed); NMR: δ3.71 (s, 3H), 3.89 (s, 2H), 4.76 (d, 2H), 6.90 (d, 2H), 7.23 (d, 2H), 7.28 (m, 5H), 7.67 (s, 1H), 7.83 (s, 1H), 8.03 (s, 1H), 8.26 (s, 1H), 8.29 (t, 1H), 9.84 (s 1H).

EXAMPLE 1(k)

2-(1-Imidazolyl)-5-phenoxymethyl-4-phenylmethylaminopyrimidine dihydrochloride

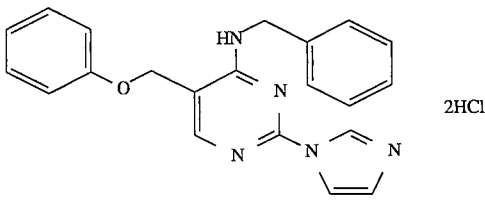

mp=179.5°–182.0° C.; NMR: δ9.92 (1 H, s), 8.60 (1H, t), 8.35 (1H, s), 8.30 (1H, s), 7.85 (1H, s), 7.50–7.20 (7H, m), 7.10–6.90 (3H, m), 5.10 (2H, s), 4.80 (2H, d).

EXAMPLE 1(l)

2-(1-Imidazolyl)-5-(1-imidazolyl)methyl-4-phenylmethylaminopyrimidine

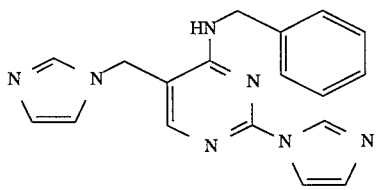

mp=202.4°–204.4° C.; NMR: δ8.40 (1H, s), 8.27 (1H, brt), 8.02 (1H, s), 7.80 (1H, s), 7.77 (1H, s), 7.36–7.15 (6H, m), 7.03 (1H, s), 6.92 (1H, s), 5.17 (2H, s), 4.69 (2H, d).

EXAMPLE 1(m)

2-(1-Imidazolyl)-5-(1-chlorovinyl)-4-phenylmethylaminopyrimidine hydrochloride

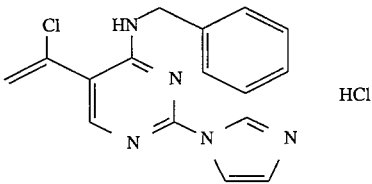

mp=97.0°–100.0° C.; NMR: δ9.80 (1H, s), 8.42 (1H, t), 8.20 (1H, s), 8.19 (1H, s), 7.80 (1 H, s), 7.40 (2H, d), 7.30 (2H, t), 7.25 (1H, t), 5.90 (1H, d), 5.88 (1H, d), 4.80 (2H, d).

EXAMPLE 1(n)

2-(1-Imidazolyl)-5-(2-thienyl)-4-phenylmethylaminopyrimidine hydrochloride

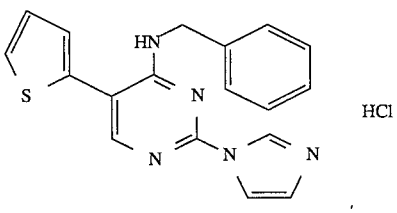

mp=91.5°–94.0° C.; NMR: δ9.85 (1H, s), 8.25 (1H, s), 8.20 (1H, s), 8.19 (1H, t), 7.82 (1H, s), 7.80 (1H, d), 7.50–7.15 (7H, m), 4.76 (2H, d)

EXAMPLE 1(o)

2-(1-Imidazolyl)-5-(2-thiazolyl)-4-phenylmethylaminopyrimidine hydrochloride

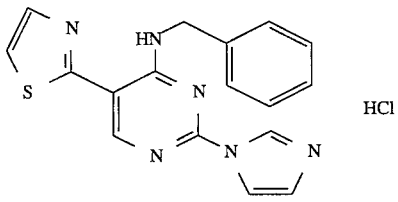

mp=167.5°–169.0° C.; NMR: δ10.20 (1H, t), 9.88 (1H, s), 8.92 (1H, s), 8.34 (1H, s), 8.03 (1H, d), 7.93 (1H, d), 7.82 (1H, s), 7.50–7.20 (5H, m), 5.00 (2H, d).

EXAMPLE 1(p)

2-(1-Imidazolyl)-5-(2-thienyl)-4-(1,3-dioxaindan-5-yl)methylaminopyrimidine hydrochloride

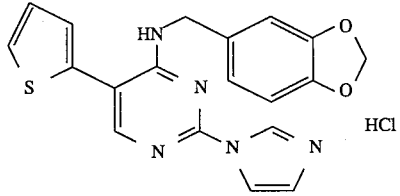

mp=100.1°–102.3° C.; NMR: δ9.88 (1H, s), 8.32 (1H, s), 8.21 (1H, s), 8.13 (1H, t), 7.84 (1H, s), 7.76 (1H, d), 7.36 (1H, d), 7.27 (1H, t), 7.03 (1H, s), 6.95 (1H, d), 6.83 (1H, d), 5.96 (2H, s), 4.46 (2H, d).

EXAMPLE 1(q)

2-(1-Imidazolyl)-5-(2-thienyl)-4-[2-(2-hydroxyethoxy)ethyl]aminopyrimidine hydrochloride

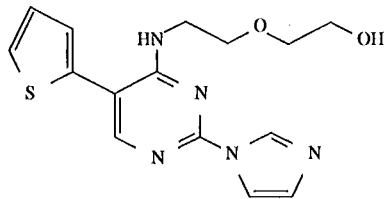

mp=127.0°–129.0° C.; NMR: δ8.52 (1H, brs), 8.12 (1H, s), 7.87 (1H, brs), 7.70 (1H, d), 7.30 (1H, d), 7.26–7.03 (3H, m), 4.62–4.53 (1H, m), 3.63 (4H, s), 3.46 (4H, s).

EXAMPLE 1(r)

2-(1-Imidazolyl)-5-(2-thienyl)-4-(1-naphthyl)methylaminopyrimidine

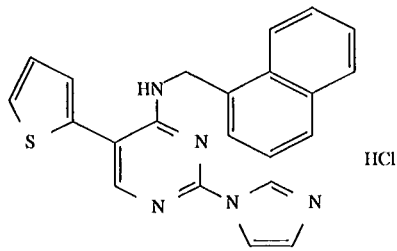

mp=132.0°–135.0° C.; NMR (CDCl3): δ9.36 (1H, s), 8.20 (1H, s), 8.09 (1H, s), 8.00–7.80 (3H, m), 7.65–7.50 (2H, m) 7.48–7.40 (4H, m), 7.18–7.09 (2H, m), 6.30–6.18 (1H, brs), 5.17 (2H, d).

EXAMPLE 1(s)

2-(1-Imidazolyl)-5-(2-thienyl)-4-(4-methoxyphenyl)methylaminopyrimidine hydrochloride

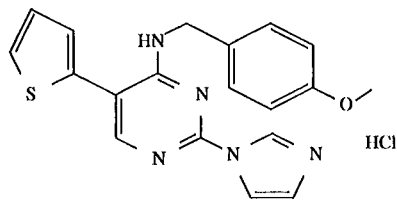

mp=167.0°–169.5° C.; NMR (CDCl3): δ9.31 (1H, s), 8.17 (1H, s), 8.11 (1H, s), 7.54–7.48 (2H, m), 7.30–7.18 (4H, m), 6.91 (2H, d), 6.28–6.15 (1H, brs), 4.67 (2H, d), 3.81 (3H, s).

EXAMPLE 1(t)

2-(1-Imidazolyl)-5-(2-thienyl)-4-(3-methoxyphenyl)methylaminopyrimidine hydrochloride

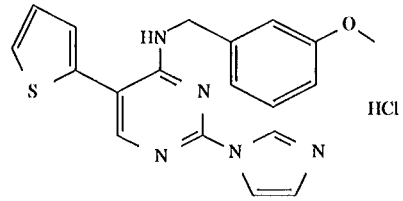

mp=153.0°–156.0° C.; NMR (CDCl3): δ9.29 (1H, s), 8.19 (1H, s), 8.08 (1H, s), 7.55–7.47 (2H, m), 7.36–7.19 (3H, m), 6.92–6.83 (3H, m), 6.32–6.21 (1H, br), 4.72 (2H, d), 3.81 (3H, s).

EXAMPLE 1(u)

2-(1-Imidazolyl)-5-(2-thienyl)-4-(2-furyl)methylaminopyrimidine hydrochloride

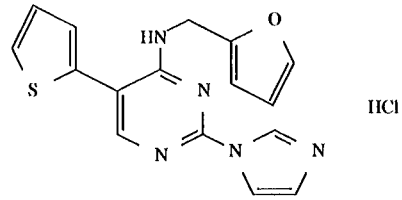

mp=158.0°–162.5° C.; NMR: δ9.96–9.70 (1H, brs), 8.45–8.20 (1H, brs), 8.24 (1H, s), 8.03 (1H, t) 7.88–7.72 (2H, m), 7.56 (1H, s), 7.35–7.31 (1H, m), 7.28–7.22 (1H, m), 6.38 (2H, s), 4.73 (2H, d).

EXAMPLE 1(v)

2-(1-Imidazolyl)-5-(2-thienyl)-4-(2-thienyl)methylaminopyrimidine hydrochloride

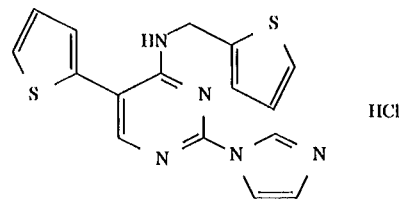

mp=151.5°–153.0° C.; NMR: δ9.96–9.75 (1H, brs), 8.46–8.17 (3H, m), 7.87–7.65 (2H, m), 7.39–7.30 (2H, m), 7.30–7.20 (1H, m), 7.16–7.11 (1H, m), 6.98–6.90 (1H, m), 4.90 (2H, d).

EXAMPLE 1(w)

2-(1-Imidazolyl)-5-(2-thienyl)-4-(3-pyridyl)methylaminopyrimidine dihydrochloride

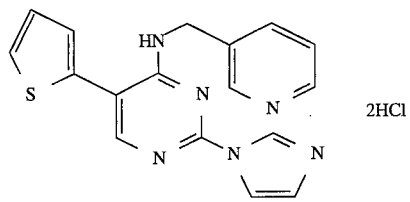

mp=165.0°–166.5° C.; NMR: δ9.94 (1H, brs), 9.04 (1H, brs), 8.77 (1H, d), 8.59 (1H, d), 8.40–8.22 (3H, m), 7.96 (1H, dd), 7.86–7.76 (2H, m), 7.44 (1H, dd)7.28 (1H, dd), 4.94 (2H, d).

EXAMPLE 1(x)

2-(1-Imidazolyl)-5-(2-thienyl)-4-(2-methoxyethyl)aminopyrimidine hydrochloride

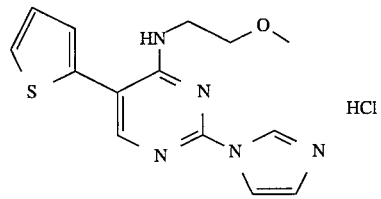

mp=139.0°–143.0° C.; NMR: δ9.77–9.65 (1H, br), 8.27 (1H, brs), 8.19 (1H, s), 7.76 (2H, d), 7.50–7.38 (1H, m), 7.33 (1H, d), 7.30–7.21 (1H, m), 3.78–3.63 (2H, m), 3.53 (2H, t), 3.26 (3H, s).

EXAMPLE 1(y)

2-(1-Imidazolyl)-5-(2-thienyl)-4-phenylmethoxyaminopyrimidine hydrochloride

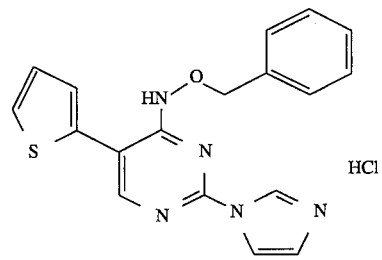

mp=155.0° C.; (decomposed) NMR: δ11.09 (1H, brs), 9.63 (1H, brs), 8.33 (1H, s), 8.21 (1H, brs), 7.80 (1H, brs), 7.75 (1H, d), 7.57–7.46 (2H, m), 7.45–7.26 (4H, m), 7.25–7.19 (1H, m), 5.02 (2H, s).

EXAMPLE 1(z)

2-(1-Imidazolyl)-5-(2-thienyl)-4-(4-chlorophenyl)methylaminopyrimidine hydrochloride

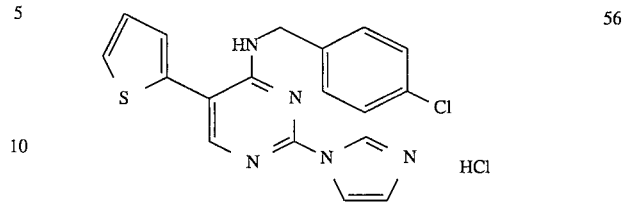

mp=129.0°–130.5° C.; NMR: δ9.96–9.65 (1H, br), 8.40–8.10 (3H, m), 7.77 (2H, dd), 7.46 (2H, d), 7.41–7.31 (3H, m), 7.30–7.23 (1H, m), 4.71 (2H, d).

EXAMPLE 1(aa)

2-(1-Imidazolyl)-5-(2-thienyl)-4-(3-chlorophenyl)methylaminopyrimidine hydrochloride

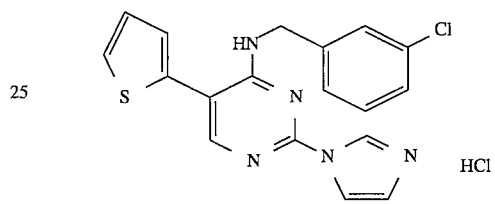

mp=101.5°–104.0° C.; NMR: δ9.92–9.67 (1H, br), 8.36–8.15 (3H, m), 7.77 (2H, dd), 7.50 (1H, s), 7.45–7.23 (5H, m), 4.73 (2H, d).

EXAMPLE 1(bb)

2-(1-Imidazolyl)-5-(2-thienyl)-4-(1,3-dioxaindan-5-yl)methylaminopyrimidine hydrochloride

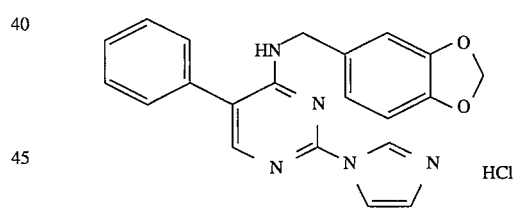

mp=119°–123° C.; NMR: δ9.83 (1H, brs), 8.32 (1H, brs), 8.07 (1H, s), 7.94 (1H, brt), 7.81 (1H, brs), 7.60–7.40 (5H, m), 7.00 (1H, s), 6.92 (1H, d), 6.82 (1H, d), 5.95 (2H, s), 4.60 (2H, d).

EXAMPLE 1(cc)

2-(1-Imidazolyl)-5-(4-methylphenyl)-4-(1,3-dioxaindan-5-yl)methylaminopyrimidine hydrochloride

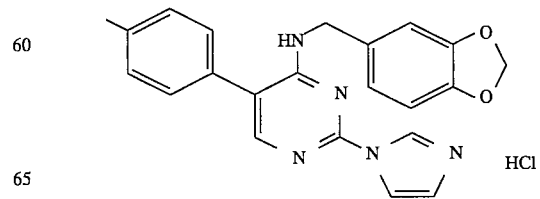

mp=125°–127.4° C.; NMR: δ9.84 (1H, s), 8.30 (1H, s), 8.04 (1H, s), 7.90 (1H, t), 7.82 (1H, s), 7.35 (4H, s), 7.00 (1H, s), 6.93 (1H, d), 6.82, (1H, d), 5.95 (2H, s), 4.60 (2H, d), 2.39 (3H, s).

EXAMPLE 1(dd)

2-(1-Imidazolyl)-5-(4-methoxyphenyl)-4-(1,3-dioxaindan-5-yl)methylaminopyrimidine hydrochloride

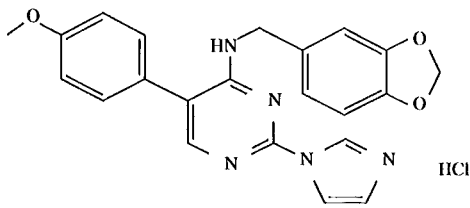

mp=207°–209° C.; NMR: δ9.84 (1H, s), 8.31 (1H, s), 8.03 (1H, s), 7.90 (1H, t), 7.82 (1H, s), 7.38 (2H, d), 7.11 (2H, d), 7.00 (1H, s), 6.93 (1H, d), 6.82 (1H, d), 5.95 (2H, s), 4.59 (2H, d), 3.83 (3H, s).

EXAMPLE 1(ee)

2-(1-Imidazolyl)-5-(5-methyl-2-thienyl)-4-(1,3-dioxaindan-5-yl)methylaminopyrimidine hydrochloride

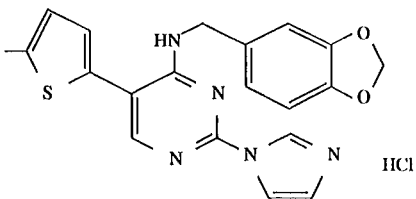

mp=180.5°–181.0° C.; NMR: δ9.88–9.66 (1H, brs), 8.32–8.23 (1H, brs), 8.14 (1H, s), 8.12–8.00 (1H, br), 7.86–7.67 (1H, br), 7.18–7.09 (1H, m), 7.07–6.78 (4H, m), 5.93 (2H, s), 4.70–4.54 (2H, br), 2.50 (3H, s).

EXAMPLE 1(ff)

2-(1-Imidazolyl)-5-(2-thienyl)-4-[4-(1-Imidazolyl)phenyl]methylaminopyrimidine dihydrochloride

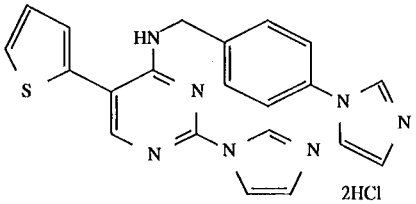

mp=173.0°–175.5° C.; NMR: δ9.86 (1H, brs), 9.78 (1H, brs), 8.42–8.20 (3H, m), 8.24 (1H, s), 7.92 (1H, brs), 7.90–7.65 (6H, m), 7.48–7.38 (1H, m), 7.38–7.25 (1H, m), 4.95–4.75 (2H, m).

EXAMPLE 1(gg)

2-(1-Imidazolyl)-5-(3-pyridyl)-4-(1,3-dioxaindan-5-yl)methylaminopyrimidine dihydrochloride

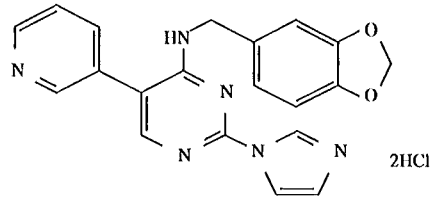

mp=162.0°–164.5° C.; NMR: δ9.96 (1H, s), 9.02 (1H, s), 8.97–8.88 (1H, m), 8.56–8.41 (2H, m), 8.36 (1H, s), 8.24 (1H, s), 8.17–8.03 (1H, m), 7.86 (1H, s), 7.01 (1H, s), 6.92 (1H, d), 6.82 (1H, d), 5.94 (2H, s), 4.62 (2H, d).

EXAMPLE 1(hh)

2-(1-Imidazolyl)-5-(3-furyl)-4-(1,3-dioxaindan-5-yl)methylaminopyrimidine hydrochloride

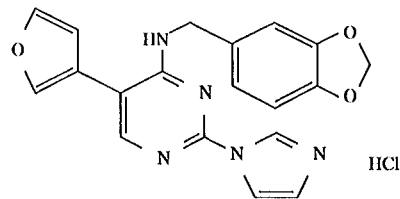

mp=106.5°–110.0° C.; NMR: δ9.80 (1H, brs), 8.28 (1H, s), 8.23 (1H, s), 8.12 (1H, s), 8.00–7.85 (2H, m), 7.79 (1H, s), 7.03 (1H, s), 6.98–6.88 (1H, m), 6.86–6.72 (2H, m), 5.94 (2H, s), 4.64 (2H, d).

EXAMPLE 1(ii)

2-(1-Imidazolyl)-5-(4-chlorophenyl)-4-(1,3-dioxaindan-5-yl)methylaminopyrimidine hydrochloride

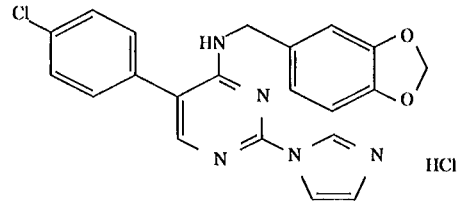

mp=109.6°–111.9° C.; NMR: δ9.83 (1H, s), 8.30 (1H, s), 8.08 (1H, s), 8.01 (1H, t), 7.80 (1H, s) 7.60 (2H, d), 7.47 (2H, d), 6.99 (1H, s), 6.92 (2H, d), 6.82 (2H, d), 5.95 ( 2H, s), 4.59 (2H, d).

EXAMPLE 1(jj)

2-(Benzimidazol-1-yl)-5-(2-thienyl)-4-(1,3-dioxaindan-5-yl)methylaminopyrimidine hydrochloride

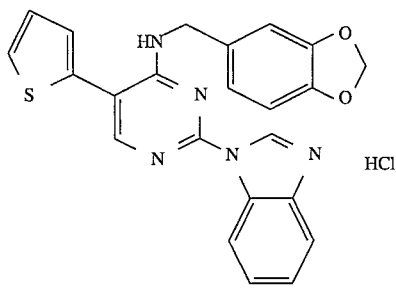

mp=155.1°–157.9° C.; NMR: δ9.65 (1H, s), 8.43 (1H, m), 8.26 (1H, s), 8.00 (1H, t), 7.80 (1H, m), 7.75 (1H, d), 7.47 (2H, m), 7.40 (1H, d), 7.28(1H, dd), 7.00 (1H, s), 6.95 (1H, d), 6.85 (1H, d), 5.96 (2H, s), 4.68 (2H, d).

EXAMPLE 1(kk)

2-(1-Imidazolyl)-5-(2-thienyl)-4-(4-ethoxycarbonylphenyl)methylaminopyrimidine hydrochloride

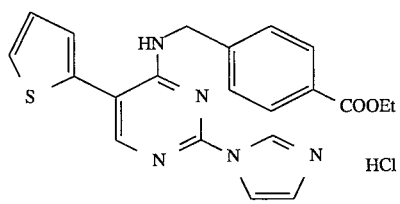

mp=97.0°–101.5° C.; NMR: δ9.71 (1H, brs), 8.32–8.18 (3H, m), 7.90 (2H, d), 7.81–7.72 (2H, m), 7.56 (2H, d), 7.43–7.37 (1H, m), 7.32–7.24 (1H, m), 4.80 (2H, d), 4.27 ( 2H, q), 1.28 (3H, t).

EXAMPLE 1(ll)

2-(1-Imidazolyl)-5-(2-naphthyl)-4-(1,3-dioxaindan-5-yl)methylaminopyrimidine hydrochloride

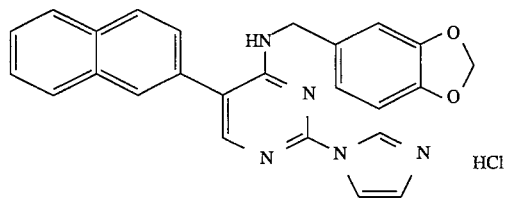

mp=117.5°–121.0° C.; NMR: δ9.87–9.77 (1H, br), 8.33 (1H, t), 8.18 (1H, s), 8.08 (2H, d), 8.04–7.94 (3H, m), 7.81 (1H, br), 7.64–7.50 (3H, m), 6.99 (1H, s), 6.92 (1H, d), 6.82 ( 1H, d), 5.94 (2H, s), 4.60 (2H, d).

EXAMPLE 1(mm)

2-(2-Methyl-1-Imidazolyl)-5-(2-thienyl)-4-(1,3-dioxaindan-5-yl)methylaminopyrimidine hydrochloride

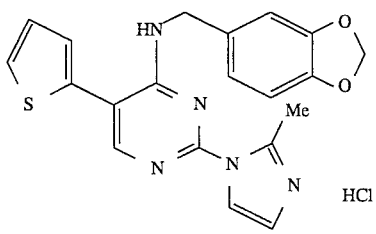

mp=214.0°–215.5° C.; NMR: δ8.25 (1H, s), 8.18 (1H, d), 8.10 (1H, t), 7.77 (1H, d), 7.70 (1H, d), 7.40 (1H, d), 7.28(1H, dd), 6.94 (1H, s), 6.84 (2H, s), 5.97 (2H, s), 4.58 ( 2H, d).

EXAMPLE 1(nn)

2-(1-Imidazolyl)-5-(2-thienyl)-4-(benzimidazol-5-yl)methylaminopyrimidine

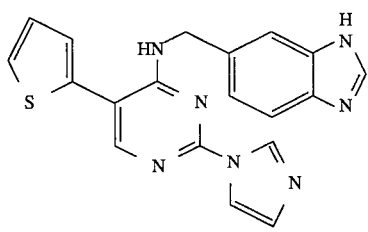

mp=65.0°–70.0° C.; NMR(CDCl3): δ8.56 (1H, brs), 8.10 (1H,s), 8.08 (1H, brs), 7.65–7.58 (2H, m), 7.39 (1H, dd), 7.29–7.20 (1H, m), 7.17–7.08 (3H, m), 6.12 (1H, br), 4.82 ( 2H, d).

EXAMPLE 1(oo)

2-(1-Imidazolyl)-5-(3-pyridyl)-4-phenylmethylaminopyrimidine dihydrochloride

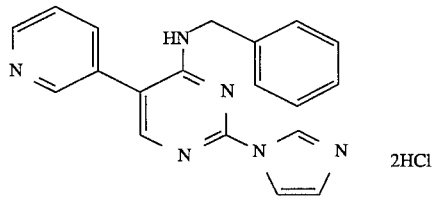

mp=184.5°–187.1° C.; NMR: δ9.97 (1H, s), 9.06 (1H, s), 8.96 (1H, d), 8.57 (2H, d), 8.34 (1H, s), 8.27 (1H, s), 8.13 (1H, t), 7.87 (1H, s), 7.43 (2H, d), 7.30 (3H, m), 4.75 (2H, d).

EXAMPLE 2

2-(3-Pyridyl)-5-(2-thienyl)-4-(1,3-dioxaindan-5-yl)methylaminopyrimidine hydrochloride

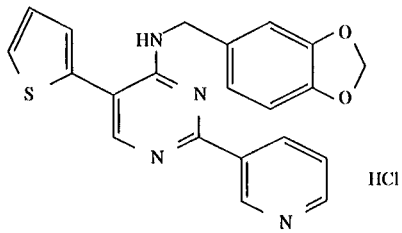

2-Chloro-5-(2-thienyl)-4-(1,3-dioxaindan-5-yl)methylaminopyrimidine (340 mg; prepared by the same procedure described in reference example 1 and 2) and tetra(triphenylphosphine)palladium (35 mg) were suspended into dimethoxyethane. In an atmosphere of argon, diethyl(3-pyridyl)boron (165 ml) and a 1N aqueous solution of sodium hydrocarbonate (2.5 ml) were added to the suspension and the mixture was refluxed for 6 hrs. The reaction mixture was cooled and evaporated. The concentrated solution was extracted with a mixture of ethyl acetate and methylene chloride. The organic layer was washed with water and a saturated brine, dried over anhydrous sodium sulfate and evaporated. The residue was purified by column chromatography on silica gel. The product was dissolved into a mixture of chloroform and methanol. To the solution, 4N hydrochloride/ethyl acetate (2 ml) was added. The mixture was concentrated to give the title compound having the following physical data.

mp=114.5°–116.5° C.; NMR: δ9.54 (1H, s), 9.18 (1H, d), 9.00 (1H, d), 8.32 (1H, s), 8.20 (1H, brt), 8.10 (1H, dd), 7.88 (1H, d), 7.88 (1H, d), 7.43 (1H, d), 7.28 (1H, dd), 7.00 (1H, s), 6.95 (1H, d), 6.85 (1H, d), 5.95 (2H, s), 4.70 (2H, d).

Reference example 3

2-Methyl-5-(2-thienyl)-4-(1,3-dioxaindan-5-yl)-methylaminopyrimidine

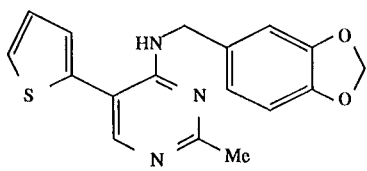

2-Methyl-5-(2-thienyl)-4-chloropyrimidine (590 mg; prepared by the same procedure as described in reference example 1) was dissolved into methylene chloride (6 ml). To the solution, (1,3-dioxaindan-5-yl)methylamine (2 ml) was added. The mixture was refluxed at 50° C. for 2 days. After reaction, the mixture was extracted with methylene chloride. The organic layer was washed with water and an aqueous saturated solution of ammonium chloride, respectively. The solution was dried over anhydrous sodium sulfate and evaporated. The residue was washed with ether to give the title compound.

EXAMPLE 3

2-[2-(3-Pyridyl)vinyl]-5-(2-thienyl)-4-(1,3-dioxaindan-5-yl)methylaminopyrimidine

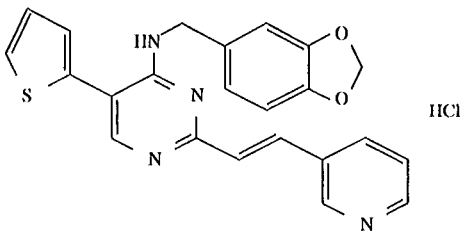

2-Methyl-5-(2-thienyl)-4-(1,3-dioxaindan-5-yl)methylaminopyrimidine (325 mg; prepared in reference example 3) and pyridine-3-aldehyde (110 mg) were dissolved into acetic acid (2 ml). The solution was refluxed for 2 days. After cooling, ethyl acetate and a saturated aqueous solution of sodium bicarbonate were added to the solution. The oily layer was washed with water and a saturated aqueous solution of sodium bicarbonate, respectively, dried over anhydrous sodium sulfate and evaporated. The residue was purified by column chromatography on silica gel. The obtained powder was dissolved in chloroform. 4N-hydrochloride/ethyl acetate (1 ml) was added to the solution and the mixture was concentrated to give the title compound having the following physical data.

mp–159.6°–161.4° C.; NMR: δ9.20 (1H, s), 8.85 (1H, d), 8.75 (1H, d), 8.28 (1H, s), 8.25 (1H, d), 8.00 (1H, dd), 7.81 (1H, d), 7.45 (1H, d), 7.42 (1H, d), 7.40 (1H, dd), 7.05(1H, s), 7.00 (2H, d), 6.88 (2H, d), 5.96 (2H, s), 4.77 (2H, s).

Formulation Example 1

The following components were admixed in conventional method and punched out to obtain 100 tablets each containing 50 mg of active ingredient.

| | |
|---|---|
| 2-(1-Imidazolyl)-4-[2-(2-hydroxyethoxy)ethyl]amino-5-(3-methoxyphenyl)-methylpyrimidine | 5.0 g |
| cellulose calcium glycolate (disintegrating agent) | 0.2 g |
| magnesium stearate (lubricating agent) | 0.1 g |
| micro crystalline cellulose | 4.7 g |

What is claimed is:
1. A 4-aminopyrimidine derivative of the formula

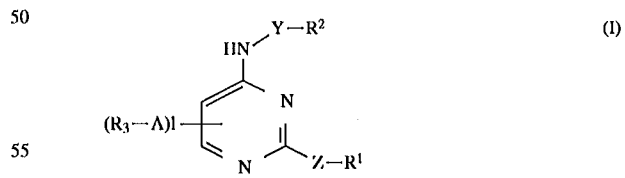

wherein A is a bond, $C_{1-4}$ alkylene or $C_{1-4}$ oxyalkylene;

Y is a bond, $C_{1-4}$ alkylene, $C_{1-4}$ alkyleneoxy, $C_{1-4}$ alkoxyphenylene or phenyl($C_{1-4}$)alkylene;

Z is a bond or vinylene;

$R^1$ is a heterocyclic ring selected from the group consisting of pyrrole, pyridine, azepine, imidazole, pyrazole, pyrimidine, pyrazine, pyridazine, benzimidazole, quinoline, isoquinoline and partially or fully saturated rings thereof;

$R^2$ is (i) a heterocyclic ring selected from the group consisting of pyrrole, pyridine, azepine, imidazole, pyrazole, pyrimidine, pyrazine, pyridazine, benzimidazole, quinoline, isoquinoline, furan, pyran, dioxole, dioxine, benzofuran, benzopyran, benzodioxole, benzodioxine, thiophene, thioine, benzothiophene, benzothione and partially or fully saturated rings thereof,
(ii) $C_{4-15}$ carbocyclic ring,
(iii) $C_{1-4}$ alkoxy,
(iv) hydroxy($C_{1-4}$ alkoxy), or
(v) hydroxy;
with the proviso that:
 when $R^1$ is pyridine or pyridine substituted by one or two of $C_{1-4}$ alkyl,
 $C_{1-4}$ alkoxy, halogen, trifluoromethyl or nitro then $R^2$ is a member selected only from the group consisting of benzodioxole or benzodioxole substituted by one or two of $C_{1-4}$ alkyl, $C_{1-4}$ alkoxy, halogen, trifluoromethyl, nitro or a group of the formula:

—COOR$^{10}$ wherein $R^{10}$ is hydrogen or $C_{1-4}$ alkyl, and hydroxy($C_{1-4}$ alkoxy);
$R^3$ is
(i) a heterocyclic ring selected from the group consisting of pyrrole, pyridine, azepine, imidazole, pyrazole, pyrimidine, pyrazine, pyridazine, benzimidazole, quinoline, isoquinoline, furan, pyran, benzofuran, benzopyran, thiophene, thioine, benzothiophene, benzothione, thiazole, isothiazole, thiazine, benzothiazole, benzoisothiazole, benzothiazine and partially or fully saturated rings thereof,
(ii) $C_{4-15}$ carbocyclic ring,
(iii) a group of formula:

$CH_2=CH(X)—$ wherein X is halogen, or
(iv) hydrogen,
l is 1 or 2,
with the proviso that:
 the ring represented by $R^1$ may be substituted by one or two of $C_{1-4}$ alkyl, $C_{1-4}$ alkoxy, halogen, trifluoromethyl or nitro;
 the ring represented by $R^2$ may be substituted by one or two of $C_{1-4}$ alkyl, $C_{1-4}$ alkoxy, halogen, trifluoromethyl, nitro or a group of the formula:

—COOR$^{10}$ wherein $R^{10}$ is hydrogen or $C_{1-4}$ alkyl, and the ring represented by $R^3$ may be substituted by one or two of $C_{1-4}$ alkyl, $C_{1-4}$ alkoxy, halogen, trifluoromethyl, nitro, cyano, ethynyl or a group of the formula:

—SONR$^7$R$^8$ wherein $R^7$ and $R^8$ are independently hydrogen or $C_{1-4}$ alkyl, and with the proviso that:
$R^2$ is not hydroxy when Y is a bond; and
$R^1$ is not bonded through its nitrogen atom when Z is vinylene,
or pharmaceutically acceptable acid addition salts thereof or pharmaceutically acceptable salts thereof.

2. A compound according to claim 1, wherein $R^1$ is heterocyclic ring selected from the group consisting of pyrrole, pyridine, azepine, quinoline, isoquinoline and partially or fully saturated rings thereof.

3. A compound according to claim 1, wherein R1 is imidazole.

4. A compound according to claim 1, wherein R1 is benzimidazole.

5. A compound according to claim 1, wherein R1 is pyridine.

6. A compound according to claim 1, wherein $R^2$ is a heterocyclic ring selected from the group consisting of pyrrole, pyridine, azepine, imidazole, pyrazole, pyrimidine, pyrazine, pyridazine, benzimidazole, quinoline, isoquinoline and partially or fully saturated rings thereof.

7. A compound according to claim 1, wherein R2 is pyridine.

8. A compound according to claim 1, wherein R2 is benzimidazole.

9. A compound according to claim 1, wherein R2 is imidazole.

10. A compound according to claim 1, wherein $R^2$ is a heterocyclic ring selected from the group consisting of furan, pyran, dioxole, dioxine, benzofuran, benzopyran, benzodioxole, benzodioxine and partially or fully saturated rings thereof.

11. A compound according to claim 1, wherein R2 is furan.

12. A compound according to claim 1, wherein R2 is 1,3-dioxaindan.

13. A compound according to claim 1, wherein $R^2$ is a heterocyclic ring selected from the group consisting of thiophene, thioine, benzothiophene, benzothione and partially or fully saturated rings thereof.

14. A compound according to claim 1, wherein R2 is thiophene.

15. A compound according to claim 1, wherein R2 is C4–15 carbocyclic ring.

16. A compound according to claim 1, wherein R2 is benzene.

17. A compound according to claim 1, wherein R2 is naphthalene.

18. A compound according to claim 1, wherein R2 is C1–4 alkoxy.

19. A compound according to claim 1, wherein R2 is hydroxy(C1–4)alkoxy.

20. A compound according to claim 1, wherein R2 is hydroxy.

21. A compound according to claim 1, wherein $R^3$ is a heterocyclic ring selected from the group consisting of pyrrole, pyridine, azepine, imidazole, pyrazole, pyrimidine, pyrazine, pyridazine, benzimidazole, quinoline, isoquinoline and partially or fully saturated rings thereof.

22. A compound according to claim 1, wherein R3 is pyridine.

23. A compound according to claim 1, wherein R3 is imidazole.

24. A compound according to claim 1, wherein $R^3$ is a heterocyclic ring selected from the group consisting of furan, pyran, benzofuran, benzopyran and partially or fully saturated rings thereof.

25. A compound according to claim 1, wherein R3 is furan.

26. A compound according to claim 1, wherein $R^3$ is a heterocyclic ring selected from the group consisting of thiophene, thioine, benzothiophene, benzothione and partially or fully saturated rings thereof.

27. A compound according to claim 1, wherein R3 is thiophene.

28. A compound according to claim 1, wherein R3 is benzthiophene.

29. A compound according to claim 1, wherein $R^3$ is a heterocyclic ring selected from the group consisting of thiazole, isothiazole, thiazine, benzothiazole, benzoisothiazole, benzothiazine and partially or fully saturated rings thereof.

30. A compound according to claim 1, wherein R3 is thiazole.

31. A compound according to claim 1, wherein R3 is C4–15 carbocyclic ring.

32. A compound according to claim 1, wherein R3 is benzene.

33. A compound according to claim 1, wherein R3 is naphthalene.

34. A compound according to claim 1, wherein R3 is a group of formula:

CH2=CH(X)— wherein X is halogen.

35. A compound according to claim 1, wherein R3-A- is hydrogen or C1–4 alkyl.

36. A compound according to claim 1, which is:
2-(1-Imidazolyl)-4-[2-(2-hydroxyethoxy)ethyl]amino-5-(3-methoxyphenyl)methylpyrimidine,
2-(1-Imidazolyl)-4-phenylmethylaminopyrimidine,
2-(1-Imidazolyl)-4-(2-methoxyethyl)aminopyrimidine,
2-(1-Imidazolyl)-5-ethyl-4-phenylmethylaminopyrimidine,
2-(1-Imidazolyl)-5-phenylmethyl-4-phenylmethylaminopyrimidine,
2-(1-Imidazolyl)-5-methyl-4-phenylmethylaminopyrimidine,
2-(1-Imidazolyl)-5,6-dimethyl-4-phenylmethylaminopyrimidine,
2-(1-Imidazolyl)-5-(3-methoxyphenyl)methyl-4-(2-methoxyethyl)aminopyrimidine,
2-(1-Imidazolyl)-5-(4-methoxyphenyl)methyl-4-[2-(2-hydroxyethoxy)ethyl]aminopyrimidine,
2-(1-Imidazolyl)-5-(4-methoxyphenyl)methyl-4-(2-methoxyethyl)aminopyrimidine or
2-(1-Imidazolyl)-5-(4-methoxyphenyl)methyl-4-phenylmethylaminopyrimidine.
2-(1-Imidazolyl)-5-phenoxymethyl-4-phenylmethylaminopyrimidine,
2-(1-Imidazolyl)-5-(1-Imidazolyl)methyl-4-phenylmethylaminopyrimidine,
2-(1-Imidazolyl)-5-(1-chlorovinyl)-4-phenylmethylaminopyrimidine,
2-(1-Imidazolyl)-5-(2-thienyl)-4-phenylmethylaminopyrimidine,
2-(1-Imidazolyl)-5-(2-thiazolyl)-4-phenylmethylaminopyrimidine,
2-(1-Imidazolyl)-5-(2-thienyl)-4-(1,3-dioxaindan-5-yl)methylaminopyrimidine,
2-(1-Imidazolyl)-5-(2-thienyl)-4-[2-(2-hydroxyethoxy)ethyl]aminopyrimidine,
2-(1-Imidazolyl)-5-(2-thienyl)-4-(1-naphthyl)methylaminopyrimidine,
2-(1-Imidazolyl)-5-(2-thienyl)-4-(4-methoxyphenyl)methylaminopyrimidine,
2-(1-Imidazolyl)-5-(2-thienyl)-4-(3-methoxyphenyl)methylaminopyrimidine,
2-(1-Imidazolyl)-5-(2-thienyl)-4-(2-furyl)methylaminopyrimidine,
2-(1-Imidazolyl)-5-(2-thienyl)-4-(2-thienyl)methylaminopyrimidine,
2-(1-Imidazolyl)-5-(2-thienyl)-4-(3-pyridyl)methylaminopyrimidine,
2-(1-Imidazolyl)-5-(2-thienyl)-4-(2-methoxyethyl)aminopyrimidine,
2-(1-Imidazolyl)-5-(2-thienyl)-4-phenylmethoxyaminopyrimidine,
2-(1-Imidazolyl)-5-(2-thienyl)-4-(4-chlorophenyl)methylaminopyrimidine,
2-(1-Imidazolyl)-5-(2-thienyl)-4-(3-chlorophenyl)methylaminopyrimidine,
2-(1-Imidazolyl)-5-(2-thienyl)-4-(1,3-dioxaindan-5-yl)methylaminopyrimidine,
2-(1-Imidazolyl)-5-(4-methylphenyl)-4-(1,3-dioxaindan-5-yl)methylaminopyrimidine,
2-(1-Imidazolyl)-5-(4-methoxyphenyl)-4-(1,3-dioxaindan-5-yl)methylaminopyrimidine,
2-(1-Imidazolyl)-5-(5-methyl-2-thienyl)-4-( 1,3-dioxaindan-5-yl)methylaminopyrimidine,
2-(1-Imidazolyl)-5-(2-thienyl)-4-[4-( 1-imidazolyl)phenyl]methylaminopyrimidine,
2-(1-Imidazolyl)-5-(3-pyridyl)-4-(1,3-dioxaindan- 5-yl)methylaminopyrimidine,
2-(1-Imidazolyl)-5-(3-furyl)-4-(1,3-dioxaindan-5-yl)methylaminopyrimidine,
2-(1-Imidazolyl)-5-(3-pyridyl)-4-phenylmethylaminopyrimidine,
2-(1-Imidazolyl)-5-(4-chlorophenyl)-4-(1,3-dioxaindan-5-yl)methylaminopyrimidine,
2-(Benzimidazol-1-yl)-5-(2-thienyl)-4-(1,3-dioxaindan-5-yl)methylaminopyrimidine,
2-(1-Imidazolyl)-5-(2-thienyl)-4-(4-ethoxycarbonylphenyl)methylaminopyrimidine,
2-(1-Imidazolyl)-5-(2-naphthyl)-4-(1,3-dioxaindan-5-yl)methylaminopyrimidine,
2-(3-Pyridyl)-5-(2-thienyl)-4-(1,3-dioxaindan-5-yl)methylaminopyrimidine,
2-[2-(3-Pyridyl)vinyl]-5-(2-thienyl)-4-(1,3-dioxaindan-5-yl)methylaminopyrimidine,
2-(2-Methyl-1-Imidazolyl)-5-(2-thienyl)-4-(1,3-dioxaindan-5-yl)methylaminopyrimidine or
2-(1-Imidazolyl)-5-(2-thienyl)-4-(benzimidazol-5-yl)methylaminopyrimidine.

37. A pharmaceutical composition which comprises, as active ingredient, an effective amount of a compound of the formula (I) depicted in claim 1 or pharmaceutically acceptable acid addition salts thereof or pharmaceutically acceptable salts thereof, with pharmaceutical carrier or coating.

38. A method for the prevention and/or the treatment of thrombosis, arteriosclerosis, ischemic heart diseases, gastric ulcer or hypertension, which comprises the administration of an effective amount of a compound of the formula (I) depicted in claim 1 or pharmaceutically acceptable salts thereof.

* * * * *